(12) United States Patent
Brauon et al.

(10) Patent No.: US 12,226,096 B2
(45) Date of Patent: Feb. 18, 2025

(54) TISSUE ANCHOR HANDLING SYSTEMS AND METHODS

(71) Applicant: Valtech Cardio Ltd., Caesarea (IL)

(72) Inventors: Haim Brauon, Beit Dagan (IL); Ehud Aviv, Costa Mesa, CA (US); Brian Patrick Murphy, Costa Mesa, CA (US); Praveen De Silva, Irvine, CA (US); Kevin K. Dang, Garden Grove, CA (US); Omar Fawzi Azanki, Rancho Santa Margarita, CA (US); Tomer Golan, Laguna Hills, CA (US); Aaron Anan Ness, Stamford, CT (US); Tal Reich, Moledet (IL); Luis Molina, Corona, CA (US); Sam Shafigh, Mission Viejo, CA (US)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 411 days.

(21) Appl. No.: 17/528,897

(22) Filed: Nov. 17, 2021

(65) Prior Publication Data

US 2022/0071620 A1 Mar. 10, 2022

Related U.S. Application Data

(63) Continuation of application No. PCT/IB2020/000472, filed on May 8, 2020.
(Continued)

(51) Int. Cl.
*A61B 17/04* (2006.01)
*A61B 90/53* (2016.01)

(52) U.S. Cl.
CPC ...... *A61B 17/0487* (2013.01); *A61B 17/0485* (2013.01); *A61B 2017/0409* (2013.01); *A61B 90/53* (2016.02)

(58) Field of Classification Search
CPC . A61B 17/04; A61B 17/0487; A61B 17/0488; A61B 90/53
See application file for complete search history.

(56) References Cited

U.S. PATENT DOCUMENTS

| 3,604,488 A | 9/1971 | Wishart et al. |
| 3,656,185 A | 4/1972 | Carpentier |

(Continued)

FOREIGN PATENT DOCUMENTS

| CN | 113331995 A | 9/2021 |
| EP | 1034753 A1 | 9/2000 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Tan-Uyen T Ho
*Assistant Examiner* — Khoa Tan Le
(74) *Attorney, Agent, or Firm* — Thomas C. Richardson

(57) ABSTRACT

An apparatus is provided for use with a tissue anchor and an anchor driver. The apparatus includes a housing, shaped to define a channel. The channel includes (i) an anchor-storage zone, and (ii) a proximal opening configured to provide access for the anchor driver to the anchor-storage zone. The channel is configured to enable sliding of the tissue anchor therewithin to be stored in the anchor-storage zone. The apparatus also includes a retaining member, shaped to define a cradle for cradling and holding the tissue anchor in the anchor-storage zone. The retaining member includes a pillar pivotable with respect to the cradle, and configured to support the tissue anchor at the cradle. Other embodiments are also described.

25 Claims, 16 Drawing Sheets

Related U.S. Application Data

(60) Provisional application No. 62/853,850, filed on May 29, 2019.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |

(56) References Cited

U.S. PATENT DOCUMENTS

| | | |
|---|---|---|
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |

(56) References Cited

U.S. PATENT DOCUMENTS

| | | |
|---|---|---|
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,403,138 B2 * | 3/2013 | Weisshaupt ........ A61B 17/1222 206/340 |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0167062 A1 | 9/2003 | Gambale et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0106950 A1 | 6/2004 | Grafton et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |

(56) References Cited

U.S. PATENT DOCUMENTS

| | | |
|---|---|---|
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0251177 A1 | 11/2005 | Saadat et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0119871 A1* | 5/2007 | Garcia ............... A61B 17/865 222/325 |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0033460 A1 | 2/2008 | Ziniti et al. |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |

(56) References Cited

U.S. PATENT DOCUMENTS

| | | |
|---|---|---|
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van Der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0053642 A1 | 3/2012 | Lozier et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0218206 A1 | 8/2013 | Gadlage |

(56) References Cited

U.S. PATENT DOCUMENTS

| | | |
|---|---|---|
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163615 A1 | 6/2014 | Gadlage et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0030034 A1 | 2/2016 | Graul et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0256274 A1 | 9/2016 | Hayoz |
| 2016/0262755 A1* | 9/2016 | Zipory .................. A61B 50/30 |
| 2016/0302917 A1 | 10/2016 | Schewel |
| 2016/0317302 A1 | 11/2016 | Madjarov et al. |
| 2016/0346084 A1 | 12/2016 | Taylor et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0020631 A1 | 1/2017 | Horras |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0185025 A1 | 7/2018 | Gorek et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0133582 A1 | 5/2019 | Eaves et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015810 A1 | 1/2020 | Piccirillo |
| 2020/0015971 A1 | 1/2020 | Brauon et al. |
| 2020/0178956 A1 | 6/2020 | Mitelberg et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0052387 A1 | 2/2021 | Greenan et al. |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |
| 2023/0218291 A1 | 7/2023 | Zarbatany et al. |
| 2023/0320856 A1 | 10/2023 | Zarbatany et al. |
| 2024/0099736 A1 | 3/2024 | Elsheikh et al. |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2010000454 A1 | 1/2010 |
| WO | 2012176195 A3 | 3/2013 |
| WO | 2014064964 A1 | 5/2014 |
| WO | 2015059699 A2 | 4/2015 |
| WO | 2017075548 A1 | 5/2017 |
| WO | 2018075879 A1 | 4/2018 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |

(56) References Cited

FOREIGN PATENT DOCUMENTS

| | | |
|---|---|---|
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.
Ahmadi, Ali et al. "Percutaneously adjustable pulmonary artery band." The Annals of thoracic surgery 60 (1995): S520-S522.
Alfieri et al."Novel Suture Device for Beating-Heart Mitral Leaflet Approximation", Ann Thorac Surg. 2002, 74:1488-1493.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. Ring+String, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
O'Reilly S et al., "Heart valve surgery pushes the envelope," Medtech Insight 8(3): 73, 99-108 (2006).
Odell JA et al., "Early Results o4yf a Simplified Method of Mitral Valve Annuloplasty," Circulation 92:150-154 (1995).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

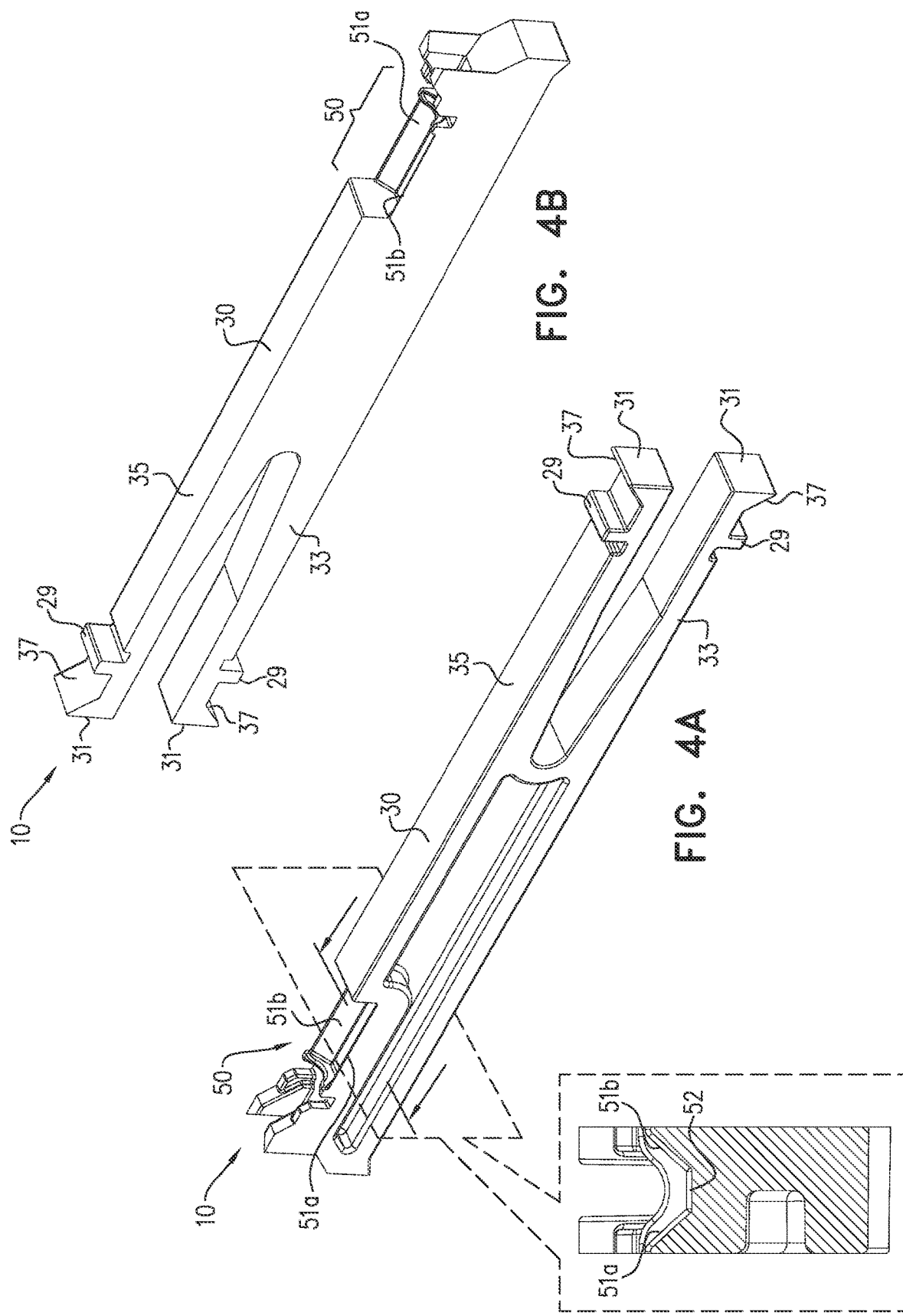

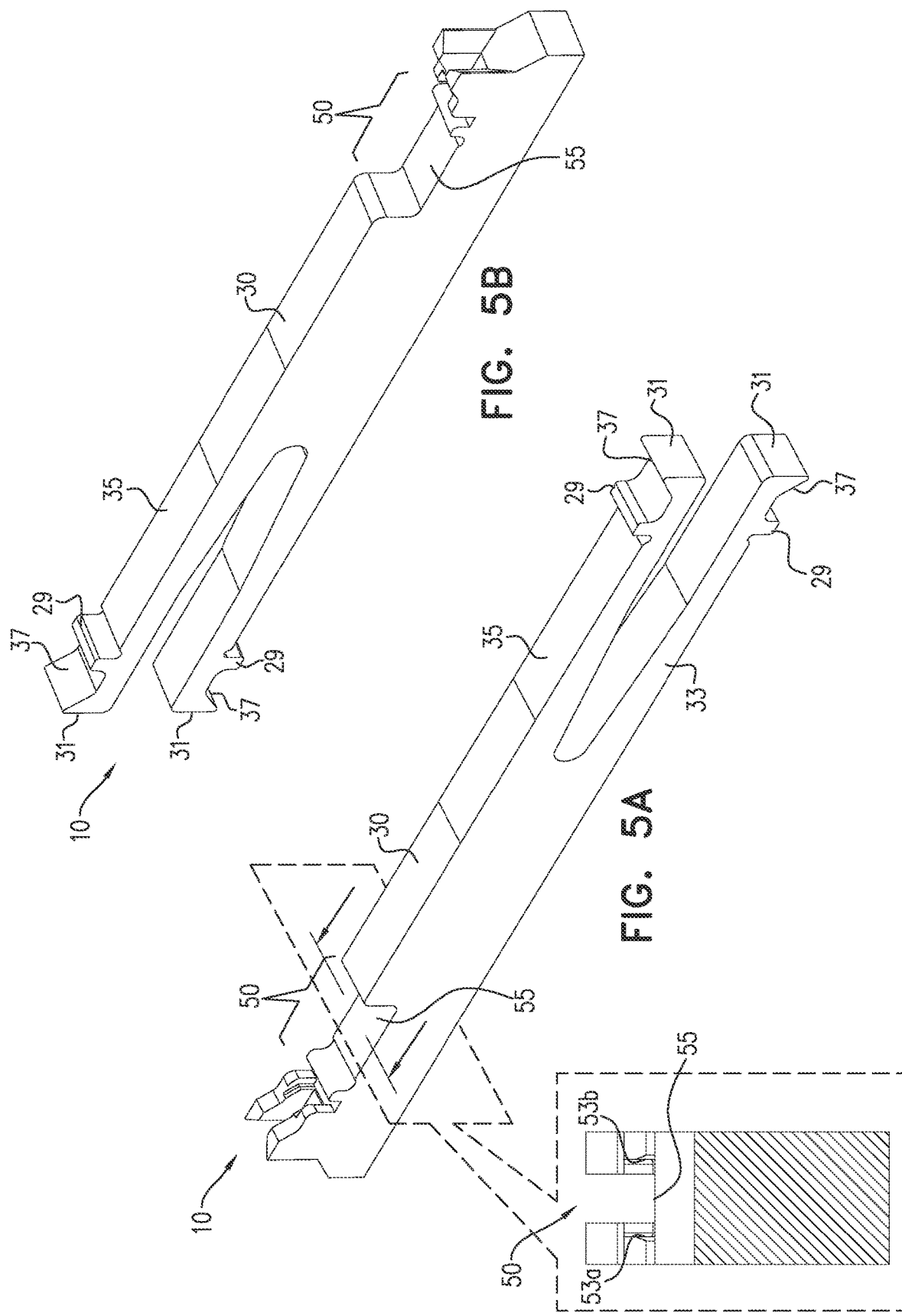

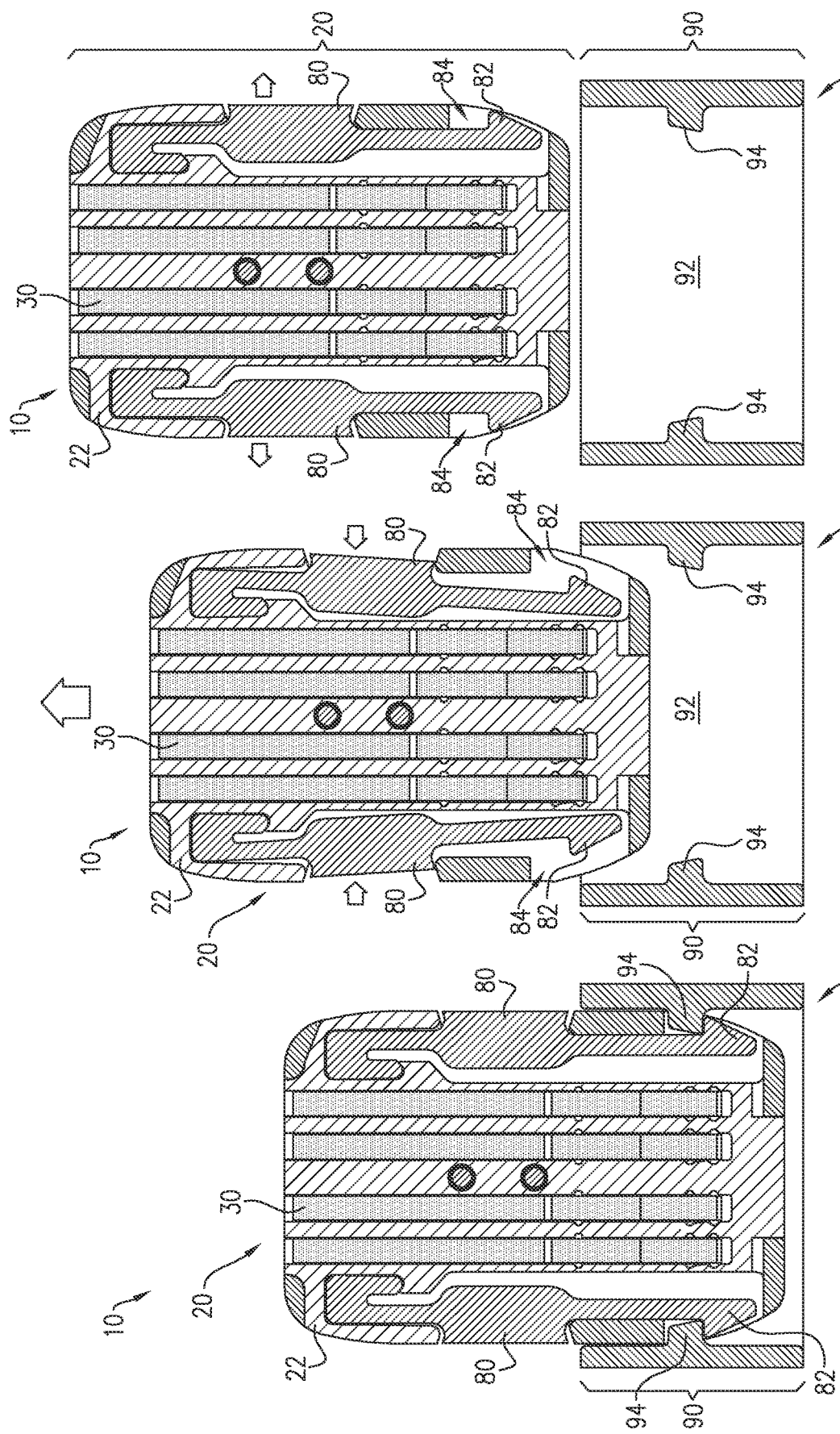

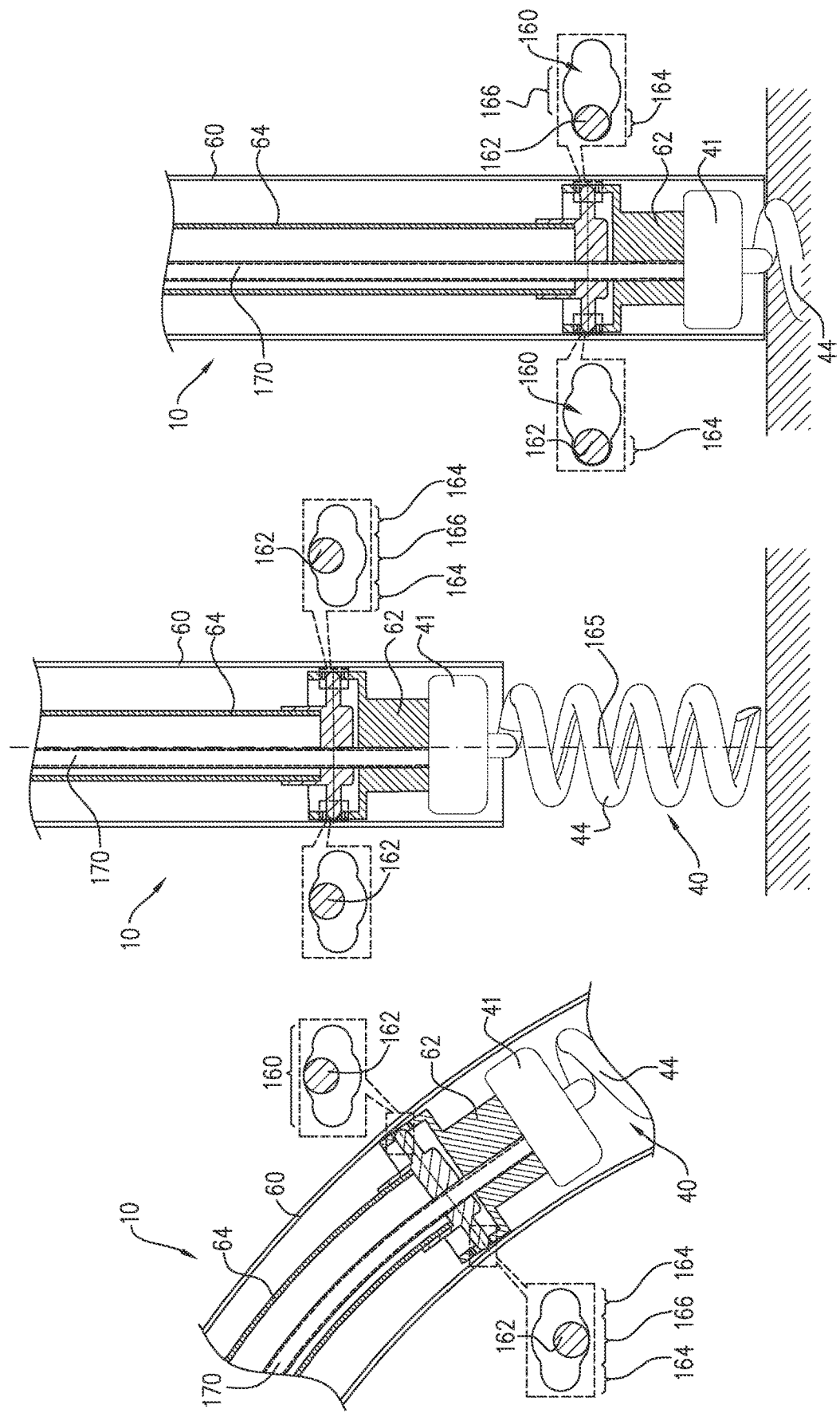

TISSUE ANCHOR HANDLING SYSTEMS AND METHODS

CROSS-REFERENCE TO RELATED APPLICATIONS

The present application is a Continuation of International Patent Application PCT/IB2020/000472 to Brauon et al., filed May 8, 2020, entitled "Tissue anchor handling systems and methods," which claims priority from U.S. Provisional Patent Application 62/853,850 to Brauon et al., filed May 29, 2019, entitled "Tissue anchor handling systems and methods," which is assigned to the assignee of the present invention and is incorporated herein by reference for all purposes.

BACKGROUND

Tissue anchors may be needed for various medical procedures. And these tissue anchors need to be easily accessible to facilitate handling of the tissue anchors during a medical procedure. There is a need for improved designs of tissue anchor holders and magazines and apparatuses that make the tissue anchors more easily accessible and usable.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. The description herein relates to systems, assemblies, methods, devices, apparatuses, combinations, etc. that may be utilized to anchor something to tissue. Various features and steps as described elsewhere in this disclosure may be included in the examples summarized here. The methods, operations, steps, etc. described herein can be performed on a living animal or on a non-living cadaver, cadaver heart, simulator (e.g. with the body parts, tissue, etc. being simulated), etc.

An anchor-handling device is configured to facilitate handling of one or more tissue anchors. The tissue anchors herein can take a variety of different configurations, shapes, and/or sizes. The anchor-handling device retains the anchors within an anchor-storage zone of a channel and/or storage area or space defined by a housing until a tool such as an anchor driver is used to retrieve the anchor. The tool is advanced through the channel and/or storage area, coupled to the anchor, and removed proximally out of the channel and/or storage area with the anchor. The anchor-handling device can be, and in some implementations is, configured to release (e.g., dispense, etc.) the anchor only when a force (e.g., a proximally-directed force) applied by the tool to the anchor is greater than a pre-defined threshold force (i.e., is sufficient), so as to prevent inadvertent exit of the anchor.

In some implementations, a retaining member is configured to retain the tissue anchor in the anchor-storage zone. The sufficient force or sufficient proximally-directed force moves the retaining member out of the way of the anchor, e.g., by moving the anchor to move the retaining member.

A wearable article can be, and in some implementations is, coupled to a holder that is shaped so as to define a space for receiving the anchor-handling device. The holder is shaped so as to define a housing, e.g., a receptacle, and a coupling configured to reversibly couple the anchor-handling device to the holder. In some implementations, the wearable article is configured to temporarily affix the anchor-handling device to a body of an operating physician that is using anchor-handling device. For some applications, the wearable article comprises a band, e.g., a wrist band or a band configured to be worn around a central region of a hand or around an arm of the operating physician. For some applications, the wearable article comprises an adhesive to temporarily affix the anchor-handling device to a garment or glove of the physician.

An anchor driver used to drive a tissue anchor into tissue of a subject has a first flexible state and a second flexible state that is less flexible than the first flexible state. For some applications, the anchor driver comprises a tube that is reinforced and made rigid and less flexible by a rigid or semi-rigid shaft that advances within the tube of the anchor driver. For some applications, a mechanism is provided at the distal end portion of the anchor driver which enables an elongate element of the driver to pivot relative to an anchor-engaging head of the driver which engages the tissue anchor.

There is therefore provided, in accordance with some applications, a system and/or an apparatus for use with an anchor-handling device. The system and/or apparatus includes a holder, shaped to define a space for receiving the anchor-handling device, the holder including a coupling configured to reversibly couple the anchor-handling device to the holder; and a wearable article coupled to and/or integrated with the holder, the wearable article being configured to temporarily affix the anchor-handling device to a body of a user (e.g., an operating physician, etc.) that is using the anchor-handling device.

In an application, the system and/or apparatus includes the anchor-handling device, and the anchor-handling device includes a housing, shaped to define a channel having an anchor-storage zone and a proximal opening.

In an application, the wearable article includes an adhesive configured to temporarily affix the anchor-handling device to a garment of the operating physician.

In an application, the wearable article includes an adhesive configured to temporarily affix the anchor-handling device to a glove of the operating physician.

In an application, the wearable article includes a hook-and-loop fastener configured to temporarily affix the anchor-handling device to a garment of the operating physician.

In an application, the wearable article includes a hook-and-loop fastener configured to temporarily affix the anchor-handling device to a glove of the operating physician.

In an application, the wearable article includes a rigid material at at least a portion thereof in a vicinity of the holder.

In an application, the wearable article includes a thin metal sheet. In an application, the thin metal sheet is malleable.

In an application, the system and/or apparatus includes an articulatable coupling configured to couple the holder to the wearable article in a manner in which the holder is articulatable relative to the wearable article.

In an application, the articulatable coupling includes a swivel coupling. In an application, the band includes a shape-memory material.

In an application, the wearable article includes a band. In an application, the at least a portion of the band includes a stretchable and flexible material. In an application, the band includes a wristband.

In an application, the band includes a first portion including a stretchable and flexible material and a second portion including a material that is less stretchable and less flexible than the stretchable and flexible material of the first portion.

In an application, the second portion is in a vicinity of the holder.

In an application, the band is shaped to define first and second ends.

In an application, the band includes a clasp which reversibly fastens the first and second ends of the band. In an application, the band includes a magnet which reversibly fastens the first and second ends of the band.

In an application, the band includes at least one spring configured to expand and contract a portion of the band.

In an application, at least a portion of the band is rigid.

In an application, the at least the portion is in a vicinity of the holder.

In an application, the band is shaped to define a closed loop.

In an application, the at least the portion of the band includes a stretchable and flexible material.

In an application, the band includes a first portion including a stretchable and flexible material and a second portion including a material that is less stretchable and less flexible than the stretchable and flexible material of the first portion.

In an application, the second portion is in a vicinity of the holder.

In an application, the band includes at least one spring configured to expand and contract a portion of the band.

In an application, at least a portion of the band is rigid.

In an application, the coupling includes a male coupling configured to protrude into the space defined by the holder.

In an application, the coupling includes a detent.

In accordance with some applications, a system and/or an apparatus (e.g., the system and/or apparatus described above or another apparatus or system herein) includes an anchor-handling device (e.g., the anchor handling device described above or another anchor handling device herein).

The anchor-handling device includes a housing, shaped to define a channel and/or storage area/storage space having an anchor-storage zone and a proximal opening.

In an application, the anchor-handling device is shaped so as to define a female coupling, the female coupling being configured to receive the male coupling of the holder in order to facilitate reversible locking of the anchor-handling device to the holder.

In an application, the anchor-handling device includes a detent, the detent being movable responsively to force applied thereto by the male coupling of the holder in order to facilitate reversible locking of the anchor-handling device to the holder.

In an application, the anchor-handling device includes a depressible element coupled to the detent, and a depressible element is pushable by the operating physician in order to apply the force to the detent.

In an application, the apparatus further includes a tissue anchor stored in the anchor-storage zone.

In an application, the tissue anchor is configured such that, while stored in the anchor-storage zone, the tissue anchor is movable out of the anchor-storage zone toward the proximal opening only in response to a proximally-directed force being applied to the tissue anchor, the proximally-directed force being greater than a pre-determined threshold force.

In an application, the tissue anchor is dimensioned to fit snugly in the anchor-storage zone.

In some applications, the system and/or apparatus further includes a retaining member. The retaining member having a longitudinal axis and having a retaining state in which the retaining member is configured to retain the tissue anchor in the anchor-storage zone. In some applications, the retaining member is also configured, by moving in response to a force (e.g., a proximally-directed force, etc.) applied to the tissue anchor, to allow the tissue anchor to leave the anchor-storage zone in response to the force (e.g., to the proximally-directed force, etc.), the force being greater than a pre-determined threshold force.

In an application, the apparatus further includes a pivot coupled to the retaining member, the pivot including a support pillar couplable to the tissue anchor, and the pivot pivots the support pillar and the tissue anchor away from the longitudinal axis of the retaining member.

In an application, the anchor is shaped so as to define a lumen, and the support pillar is shaped so as to define a rod that fits within the lumen of the tissue anchor.

In an application, the retaining member is shaped to define a cradle at a proximal end thereof, the cradle defining first and second slanted surfaces, the first and second surfaces being configured to abut against the tissue anchor such that the anchor fits snugly in the anchor-storage zone.

In an application, the first and second slanted surfaces adjoin to form an apex of the cradle. In an application, the first and second slanted surfaces form a generally "V"-shape.

In some applications: the housing is configured to define a plurality of channels, each of the plurality of channels having a respective anchor-storage zone/area and a respective proximal opening. The system/apparatus can include a plurality of tissue anchors, slidable through a respective channel and configured to be stored in a respective anchor-storage zone/area.

In some applications, the system and/or apparatus includes a plurality of retaining members (e.g., in the housing), each retaining member configured to retain a respective tissue anchor in the respective anchor-storage zone, and to allow the respective tissue anchor to leave the respective anchor-storage zone in response to a force, such as a proximally-directed force, applied to the respective tissue anchor.

In an application, the apparatus further includes an anchor driver, and in the retaining state, the anchor driver is slidable through at least a part of the channel and reversibly lockable to the tissue anchor.

In some applications, the housing is shaped to define a chamber that is in fluid communication with the channel, the chamber having a longitudinal axis, and at least part of the retaining member is configured to slide within the chamber in response to the force or proximally-directed force applied to the tissue anchor.

In an application, the retaining member includes a pin, configured to slide through the chamber.

In some applications, the housing is shaped to define first and second cavities that are in fluid communication with the chamber. At least a portion of the retaining member can be resilient. The pin can be shaped so as to define first and second legs that are compressible toward each other and toward the longitudinal axis of the chamber, each of the first and second legs being shaped to define a respective detent.

In an application, the system/apparatus is dimensioned such that when the retaining member allows the tissue anchor to leave the anchor-storage zone, further proximal movement of the retaining member causes the respective detents of the first and second legs to move into the respective first and second cavities.

In an application, the first and second cavities and the respective detents of the first and second legs are dimensioned such that when each detent is disposed within the respective first and second cavities, a distally-directed force required to return the apparatus to the retaining state is more than twice as great as the threshold force.

In some applications, the housing is shaped to define first and second cavities that are in fluid communication with the chamber. At least a portion of the retaining member can be resilient. In an application, the pin is shaped so as to define first and second legs that are compressible toward each other and toward the longitudinal axis of the chamber, each of the first and second legs being shaped to define a respective detent. In the retaining state, the resilience of at least the portion of the retaining member can be configured to hold the detents of the first and second legs within the respective first and second cavities. In an application, the retaining member is configured to deform in response to the force or proximally-directed force applied to the tissue anchor, such that the first and second legs compress toward each other and the respective detents of the first and second legs exit the respective first and second cavities.

In some applications the housing is shaped to define third and fourth cavities that are in fluid communication with the chamber. The apparatus can be dimensioned such that when the retaining member allows the tissue anchor to leave the anchor-storage zone, further proximal movement of the retaining member causes the respective detents of the first and second legs to move into the respective third and fourth cavities.

In some applications, the third and fourth cavities and the respective detents of the first and second legs are dimensioned such that when each detent is disposed within the respective third and fourth cavities, a distally-directed force required to return the apparatus to the retaining state is more than twice as great as the threshold force.

In some applications, the anchor driver includes, at a distal end thereof, an anchor-engaging head introducible through the opening of the housing and actuatable to be reversibly coupled to the tissue anchor. The anchor driver includes, at a proximal end thereof, a handle including an adjuster configured to actuate the anchor-engaging head. In an application, the anchor driver can also include an elongate advanceable element disposed between the distal end of the anchor driver and the proximal end of the anchor driver, and configured to be transcatheterally advanced through vasculature of a subject. In an application, the elongate advanceable element is flexible.

In an application, the anchor-engaging head has a longitudinal axis, and the head is shaped so as to define a tissue-anchor engaging slot configured to engage a proximal end of the tissue anchor, the slot being angled at a nonzero angle with respect to the longitudinal axis.

In an application, the anchor-engaging head is articulatable with respect to the elongate advanceable element.

In an application, the apparatus further includes a coupling pin coupled to a distal end of the elongate advanceable element, and the anchor-engaging head is shaped so as to define at least one slotted opening, and the coupling pin is moveable within the slotted opening to facilitate articulating between the anchor-engaging head and the elongate advanceable element.

In an application, the slotted opening is shaped so as to define an extreme section and a main section that is wider than the extreme section, and when the coupling pin is disposed within the extreme section, movement of the anchor-engaging head with respect to the elongate advanceable element is restricted, and when the coupling pin is disposed within the main section, movement of the anchor-engaging head with respect to the elongate advanceable element is facilitated.

In an application, the elongate advanceable element includes a flexible tube shaped so as to define a lumen, and the apparatus further includes a shaft slidable with respect to the flexible tube in order to control a flexibility of the flexible tube.

In an application, the shaft is more rigid than the flexible tube.

In an application, the elongate advanceable element has a first flexible state and a second flexible state that is less flexible than the first flexible state, and the elongate advanceable element assumes the second flexible state when the shaft is positioned within the lumen of the flexible tube.

There is further provided, in accordance with some applications, a method, including temporarily affixing to a body of an operating physician a wearable article coupled to a holder shaped to define a space for receiving an anchor-handling device, the holder including a coupling configured to reversibly couple the anchor-handling device to the holder; and reversibly coupling the anchor-handling device to the holder.

In an application, the wearable article includes an adhesive, and temporarily affixing includes temporarily affixing the anchor-handling device to a garment of the operating physician.

In an application, the wearable article includes an adhesive, and temporarily affixing includes temporarily affixing the anchor-handling device to a glove of the operating physician.

In an application, the wearable article includes a hook-and-loop fastener, and temporarily affixing includes temporarily affixing the anchor-handling device to a garment of the operating physician.

In an application, the wearable article includes a hook-and-loop fastener, and temporarily affixing includes temporarily affixing the anchor-handling device to a glove of the operating physician.

In an application, the wearable article includes a thin metal sheet, and temporarily affixing includes shaping the thin metal sheet to conform to a portion of the body of the operating physician.

In an application, the method further includes articulating the holder with respect to the wearable article.

In an application, the method further includes swiveling the holder with respect to the wearable article.

In an application, the wearable article includes a band, and temporarily affixing includes positioning at least a portion of the band around a portion of the body of the operating physician.

In an application, positioning includes positioning the at least the portion of the band around a central region of a hand of the operating physician. In an application, positioning includes positioning the at least the portion of the band around a wrist of the operating physician.

In an application, positioning the at least the portion includes sliding the band around a central region of a hand of the operating physician.

This method, including its individual steps, can be performed as part of a training or simulation.

There is further provided, in accordance with some applications, a system and/or an apparatus for use with a tissue anchor. The system/apparatus including an anchor driver. In some applications, the anchor driver includes an anchor coupling element (e.g., an anchor-engaging head, etc.) configured to reversibly couple the tissue anchor to the anchor driver.

In some applications, an elongate advanceable element is coupled at a distal end thereof to the anchor coupling element, the elongate advanceable element having a distal end portion. In some applications, the anchor driver also has a distal end portion, and the distal end portion of the anchor driver has a first flexible state and a second flexible state that is less flexible than the first flexible state.

In an application, when the distal end portion of the anchor driver is in the first flexible state, the anchor-engaging head is configured to pivot with respect to the distal end portion of the elongate advanceable element.

In an application, the elongate advanceable element is shaped so as to define a flexible tube having a lumen, and the apparatus further includes a shaft slidable with respect to the flexible tube in order to control a flexibility of the flexible tube.

In an application, the shaft is more rigid than the flexible tube.

In an application, the shaft is slidable within the lumen of the flexible tube such that the distal end portion of the anchor driver assumes the second flexible state, and the shaft is retractable from within the lumen of flexible tube at at least the distal end portion of the elongate advanceable element distally, such that the distal end portion of the anchor driver assumes the first flexible state.

In an application, the anchor-engaging head is articulatable with respect to the elongate advanceable element.

In an application, the system and/or apparatus further includes a coupling pin coupled to a distal end of the elongate advanceable element, and the anchor-engaging head is shaped so as to define at least one slotted opening, and the coupling pin and the slotted opening are moveable with respect to each other in order to facilitate articulating between the anchor-engaging head and the elongate advanceable element.

In an application, the slotted opening is shaped so as to define at least one extreme section and a main section that is wider than the extreme section, and when the coupling pin is disposed within the extreme section, movement of the anchor-engaging head and the elongate advanceable element with respect to each other is restricted and the distal end portion of the anchor driver assumes the second flexible state. Also, in some applications, when the coupling pin is disposed within the main section, movement of the anchor-engaging head and the elongate advanceable element with respect to each other is facilitated and the distal end portion of the anchor driver assumes the first flexible state.

In an application, the main section has a first width that is 1.5-2 times wider than the extreme section.

In an application, the elongate advanceable element is rotatable about a longitudinal axis of the distal end portion of the elongate advanceable element with respect to the anchor-engaging head so as to transition the coupling pin between the main section and the extreme section.

There is further provided, in accordance with some applications, a method, including reversibly engaging an anchor-engaging head of an anchor driver with a tissue anchor. The anchor driver and tissue anchor can be the same as or similar to other anchor drivers and tissue anchor described herein. In some implementations, the anchor driver includes an elongate advanceable element coupled at a distal end thereof to the anchor coupling element, the elongate advanceable element having a distal end portion. In some implementations, the anchor driver has a distal end portion that has a first flexible state and a second flexible state that is less flexible than the first flexible state.

The method can also include, subsequently to the engaging, transitioning the distal end portion of the anchor driver to the first flexible state.

In an application, prior to the engaging the anchor-engaging head of the anchor driver with the tissue anchor, transitioning the distal end portion of the anchor driver from the first flexible state to the second flexible state.

In an application, during the engaging, the distal end portion is in the second flexible state, and transitioning includes transitioning the distal end portion of the anchor driver from the second flexible state to the first flexible state.

In an application, the method further includes disengaging the anchor-engaging head from the tissue anchor, and during the disengaging, the distal end portion of the anchor driver is in the second flexible state.

In an application, when the distal end portion of the anchor driver is in the first flexible state, pivoting the anchor-engaging head and the distal end portion of the elongate advanceable element with respect to each other.

In an application, the method further includes driving the tissue anchor into tissue of a subject (e.g., heart tissue, heart valve tissue, vasculature tissue, muscle tissue, etc.), and the method further includes applying torque to the elongate advanceable element, and, during the applying the torque, the distal end portion of the anchor driver is in the second flexible state.

In an application, the method further includes advancing the elongate advanceable element through vasculature of the subject, and, during the advancing, the distal end of the anchor driver is in the first flexible state, and, prior to the applying the torque, transitioning the distal end portion of the anchor driver from the first flexible state to the second flexible state.

In an application, the elongate advanceable element is shaped so as to define a flexible tube having a lumen, and the method further includes controlling a flexibility of the flexible tube by sliding a shaft with respect to the flexible tube.

In an application, the shaft is more rigid than the flexible tube.

In an application, the method further includes articulating the anchor-engaging head and the elongate advanceable element with respect to each other.

In an application, a distal end of the elongate advanceable element includes a coupling pin, and the anchor-engaging head is shaped so as to define at least one slotted opening, and the method further includes facilitating the articulating by facilitating movement between the coupling pin and the at least one slotted opening.

In an application, the slotted opening is shaped so as to define at least one extreme section and a main section that is wider than the extreme section, and transitioning the distal end portion of the elongate advanceable element to the first flexible state includes facilitating the movement between the coupling pin and the at least one slotted opening while the coupling pin is disposed within the main section.

The method can further include transitioning the distal end portion of the anchor driver to the second flexible state by facilitating positioning of the coupling pin within the extreme section and by the positioning restricting movement of the anchor-engaging head and the elongate advanceable element with respect to each other.

In an application, the main section has a first width that is 1.5-2 times wider than the extreme section.

In an application, the elongate advanceable element is rotatable with respect to the anchor-engaging head about a longitudinal axis of the distal end portion of the elongate advanceable element, and transitioning the distal end portion of the anchor driver to the first flexible state includes rotating the elongate advanceable element with respect to the anchor-engaging head, and by the rotating, moving the coupling pin from the extreme section to the main section.

In an application, subsequently to the transitioning of the distal end portion of the anchor driver to the first flexible state, transitioning the distal end portion of the anchor driver to the second flexible state by rotating the elongate advanceable element with respect to the anchor-engaging head, and by the rotating, moving the coupling pin from the main section to the extreme section.

In an application, moving the coupling pin from the main section to the extreme section includes locking the anchor-engaging head with respect to the distal end portion of the elongate advanceable element.

This method, including its individual steps, can be performed as part of a training or simulation, (e.g., which can involve simulated tissue, etc.).

There is further provided, in accordance with some applications, a system and/or an apparatus for use with a tissue anchor including an anchor handling device having a housing. In some applications, the anchor-handling device and/or the housing thereof is shaped to define a channel having an anchor-storage zone or area and a proximal opening.

In some applications, the anchor-handling device and/or the housing thereof includes a retaining member in the channel of the anchor-handling device. The retaining member can have a retaining state in which the retaining member is configured to retain the tissue anchor in the anchor-storage zone. In some applications, the retaining member is configured to allow the tissue anchor to leave the anchor-storage zone/area in response to a force applied thereto. In some implementations, the force is a proximally-directed force, and the retaining member is configured, by moving in response to the proximally-directed force applied to the tissue anchor, to allow the tissue anchor to leave the anchor-storage zone/area in response to the proximally-directed force. In some implementations, the proximally-directed force is greater than a pre-determined threshold force, and/or the retaining member is configured such that a pre-determined threshold force is less than a desired amount of proximally-directed force.

In some applications, the retaining member is shaped to define a cradle at a proximal end thereof, the cradle defining first and second slanted surfaces, the first and second surfaces being configured to abut against the tissue anchor such that the anchor fits snugly in the anchor-storage zone.

In an application, the first and second slanted surfaces adjoin to form an apex of the cradle.

In an application, the first and second slanted surfaces form a generally "V"-shape.

There is further provided, in accordance with some applications, a system and/or an apparatus for use with a tissue anchor, the system/apparatus including an anchor-handling device having a housing. The system/apparatus and/or housing thereof is shaped to define a channel having an anchor-storage zone/area and a proximal opening.

In some implementations, the system/apparatus and/or housing thereof includes a retaining member disposed within the channel of the anchor-handling device. In some implementations, the retaining member has a longitudinal axis and a retaining state in which the retaining member is configured to retain the tissue anchor in the anchor-storage zone. The retaining member can be configured, by moving in response to a force (e.g., a proximally-directed force, etc.) applied to the tissue anchor, to allow the tissue anchor to leave the anchor-storage zone in response to the force (e.g., a proximally-directed force, etc.). The force (e.g., the proximally-directed force, etc.) can be greater than a pre-determined threshold force, and/or the retaining member can be configured to release the tissue anchor in response to a force above a pre-determined threshold force.

In some implementations, a pivot is coupled to the retaining member, the pivot including a support pillar couplable to the tissue anchor, the pivot being configured to pivot the support pillar and the tissue anchor away from the longitudinal axis of the retaining member.

In an application, the anchor is shaped so as to define a lumen, and the support pillar is shaped so as to define a rod that fits within the lumen of the tissue anchor.

Additional features, components, steps, etc. can be incorporated into the systems, apparatuses, methods, etc. described in this summary.

The present invention will be more fully understood from the following detailed description of applications thereof, taken together with the drawings, in which:

BRIEF DESCRIPTION OF THE DRAWINGS

FIGS. 4A-B, 5A-B, and 6A-C are schematic illustrations of examples of respective pins shaped to define cradles for cradling and holding a respective tissue anchor, in accordance with some applications;

FIGS. 7A-C, 8, 9, and 10A-B are schematic illustration of an example of a wearable article coupled to a holder which holds the anchor-handling device, in accordance with some applications;

FIGS. 12, 13A-C, and 14A-B are schematic illustrations of an example of an anchor driver that is rotatably pivotable with respect to a tissue anchor, in accordance with some applications.

DETAILED DESCRIPTION OF EMBODIMENTS

Figure 1:
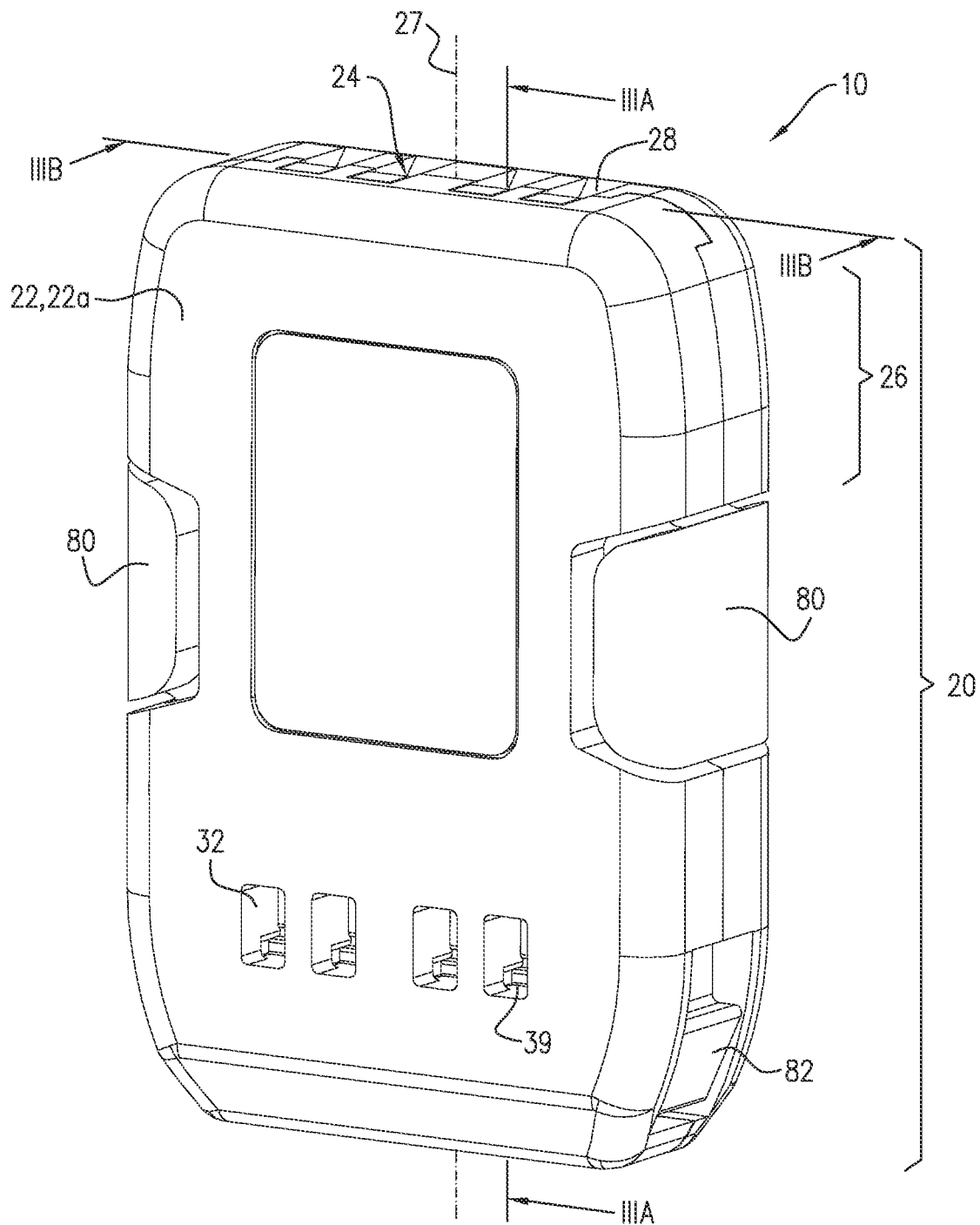
FIGS. 1-2 and 3A-C are schematic illustrations of an example of an anchor-handling device, configured to facilitate handling of at least one tissue anchor, in accordance with some applications.

Reference is made to FIGS. 1-2 and 3A-C, which are schematic illustrations of a system 10 comprising an anchor-handling device 20 (e.g., a magazine, cartridge, carrier, etc.), configured to facilitate handling of at least one tissue anchor 40, in accordance with some applications. Device 20, as shown, is configured to handle a plurality of anchors 40, and for such applications, device 20 defines a multiple-anchor-handling device. Device 20 comprises a housing 22 that defines a channel 24, an anchor-storage zone 26 (e.g., at a proximal end of the channel) and an opening 28 (e.g., at a proximal end of the channel) that provides access to the channel and the anchor-storage zone. There can be a smooth transition between anchor-storage zone 26 and channel 24. Device 20 further comprises a retaining member, such as a pin 30, which is configured to retain tissue anchor 40 in zone 26, and to stop retaining the tissue anchor in response to a sufficient force, such as a proximally-directed force, applied to the tissue anchor. That is, when a force or a proximally-directed force that is greater than a pre-determined threshold force is applied to tissue anchor 40, the retaining member stops retaining (e.g., releases) the tissue anchor.

Figure 2:
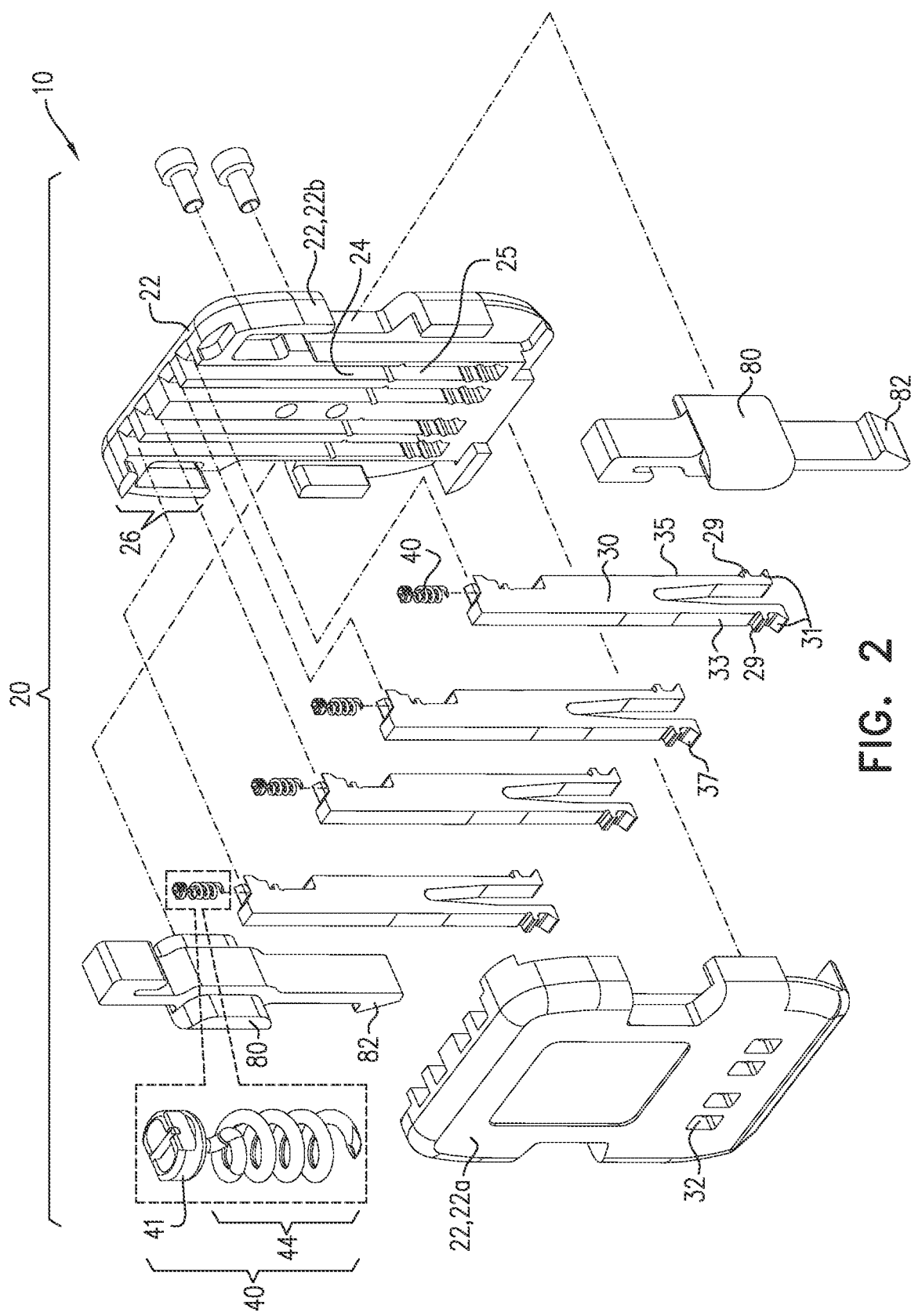

In some implementations, the retaining member (e.g., pin 30) has a retaining state in which it retains tissue anchor 40 within zone 26, and is moved out the retaining state when the sufficient proximally-directed force is applied to the tissue anchor. FIG. 1 shows, in accordance with some applications, pin 30 in a retaining state thereof, in which at least a portion 29 (e.g., a restricting portion, and/or a distal portion) of the pin is disposed within a cavity 32 (e.g., distal to anchor 40), thereby retaining the anchor in zone 26 by restricting proximal movement of the tissue anchor (described hereinbelow). As shown in FIG. 2, device 20 can comprise two housing portions 22a and 22b that are adjoined. Each housing portion 22a and 22b is shaped so as to define a plurality of cavities 32.

Housing 22 of device 20 can be shaped to define a plurality of channels 24, each of the plurality of channels having a respective anchor-storage zone/area 26 and a respective proximal opening 28. In some implementations, device 20 comprises a plurality of tissue anchors 40 slidable through a respective channel 24 and are configured to be stored in a respective anchor-storage zone/area. As such, device 20 comprises a plurality of retaining members, e.g., pins 30. Each retaining member can be configured to retain a respective tissue anchor 40 in the respective anchor-storage zone/area 26, and to allow the respective tissue anchor 40 to leave the respective anchor-storage zone/area 26 in response to a force, such as a proximally-directed force, applied to the respective tissue anchor 40.

A variety of tissue anchors, which can be of a variety of configurations, shapes, and sizes can be used. In some implementations, tissue anchor 40 is shaped so as to define a core 41 and a tissue-engaging member 44. Tissue anchor 40 can be dimensioned to fit snugly in anchor-storage zone 26 of the housing. The tissue anchor (e.g., core 41 thereof) can be dimensioned to slide snugly through channel 24 of the housing, and for some applications this snug sliding prevents tissue-engaging member 44 of the anchor from touching the housing (e.g., the wall of the channel) when the anchor moves through the channel. At least a portion of the pin can be dimensioned to slide snugly through the chamber.

Figure 3A:
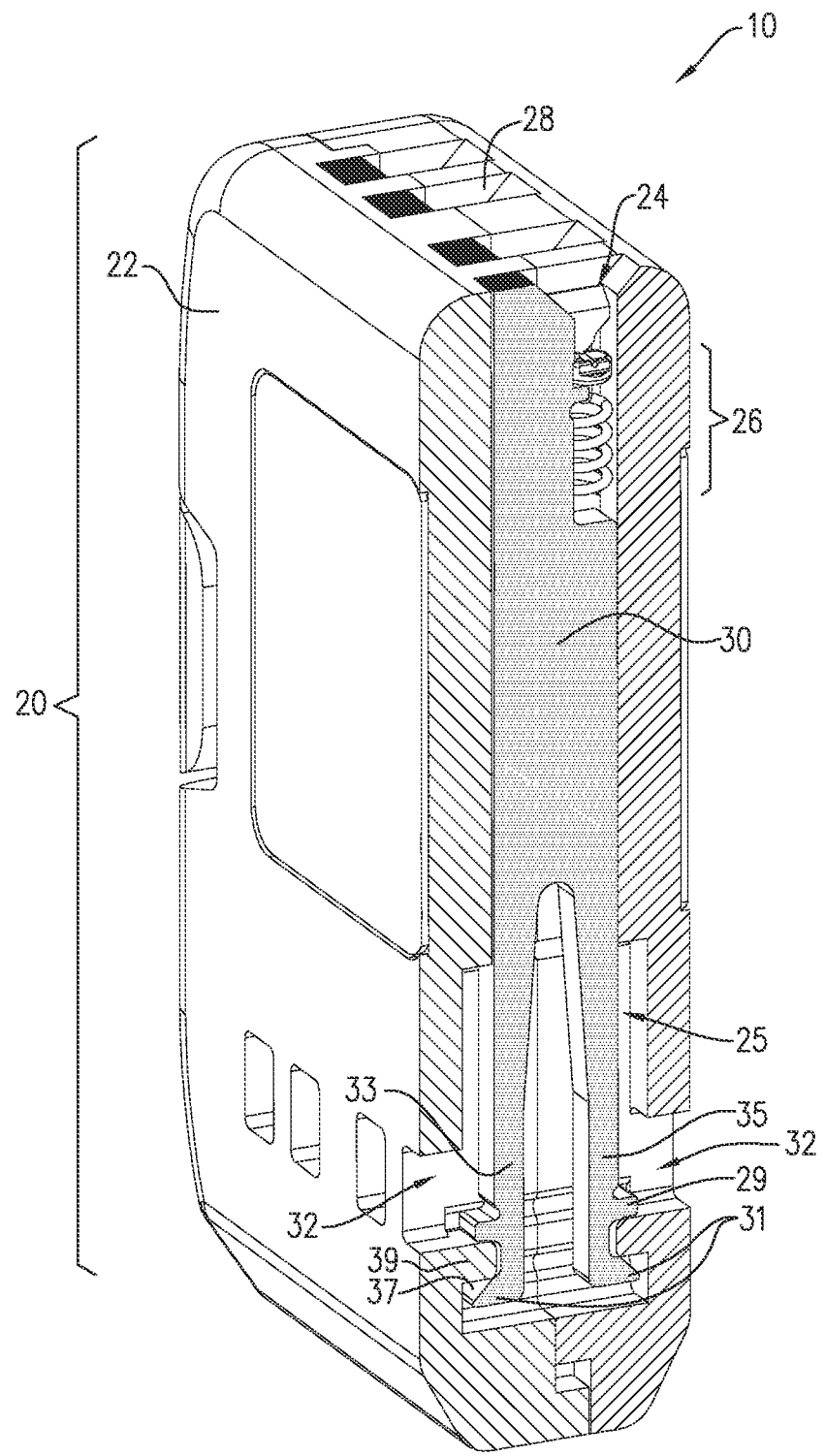
Figure 3B:
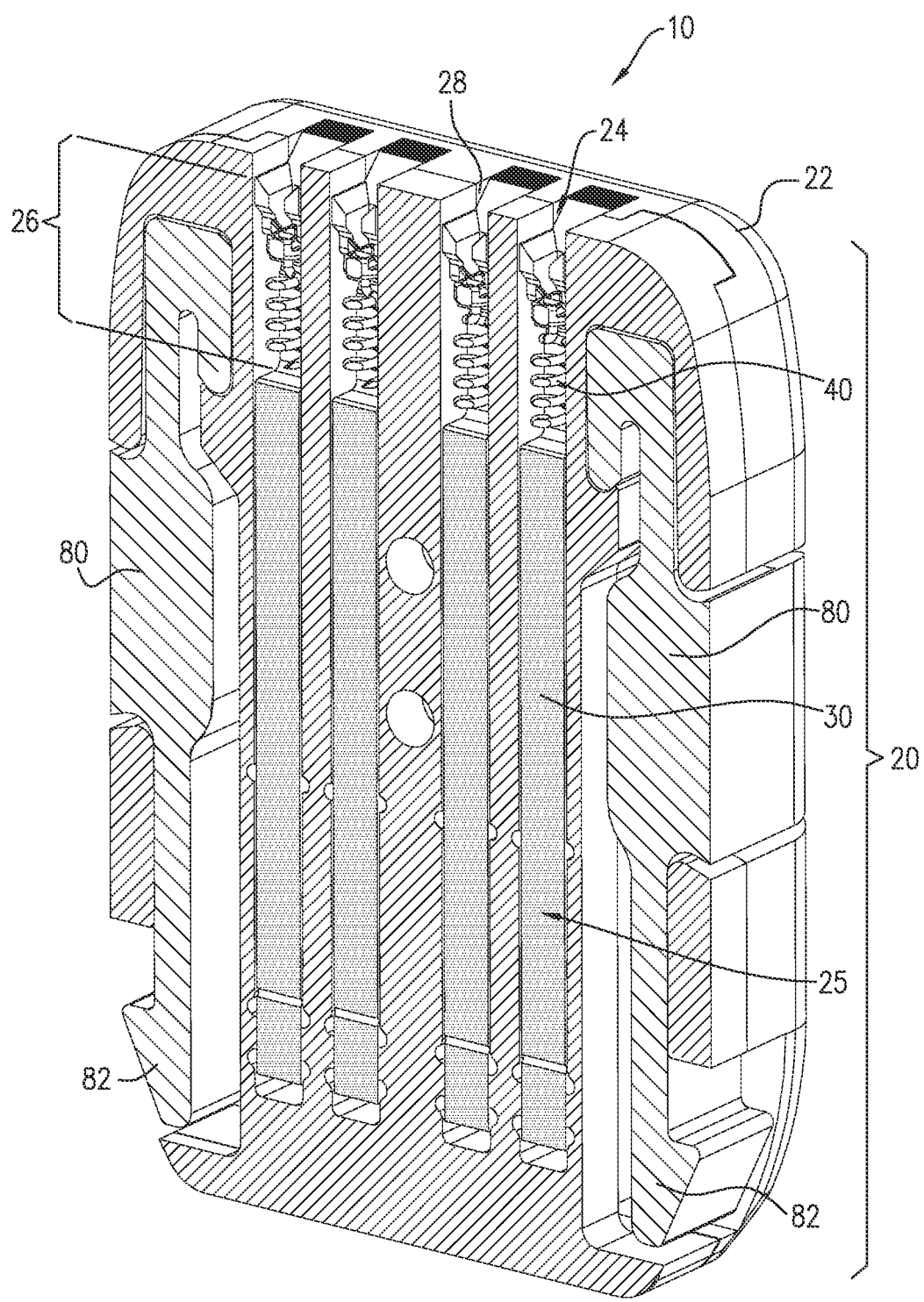

As shown in FIGS. 3A-B, the retaining member (e.g., pin 30) has a retaining state in which it retains tissue anchor 40 within zone 26. The retaining member can be moved out the retaining state when the sufficient force, such as a sufficient proximally-directed force, is applied to the tissue anchor. FIGS. 3A-B show, in accordance with some applications, pin 30 in a retaining state thereof, in which at least a distal portion of the pin is disposed within channel a chamber 25 (e.g., distal to anchor 40), thereby retaining the anchor in zone 26 by restricting proximal movement of the tissue anchor. Chamber 25 is defined by housing 22 and can be in fluid communication with channel 24 (e.g., in the absence of pin 30). In some implementations, chamber 25 has a central longitudinal axis that is parallel with a central longitudinal axis of channel 24.

It is to be noted that although pin 30 is shown as being generally rectangular (i.e., having a generally rectangular transverse cross-section), the term "pin", as used throughout the present application, including the specification and the claims, may include a pin having a different shape (e.g., having a circular transverse cross-section). Pin 30 comprises first and second legs 33 and 35 that are compressible radially inwardly and toward each other and toward a longitudinal axis 27 of channel 24 and of chamber 25 in response to application of a compression force thereto.

Figure 3C:
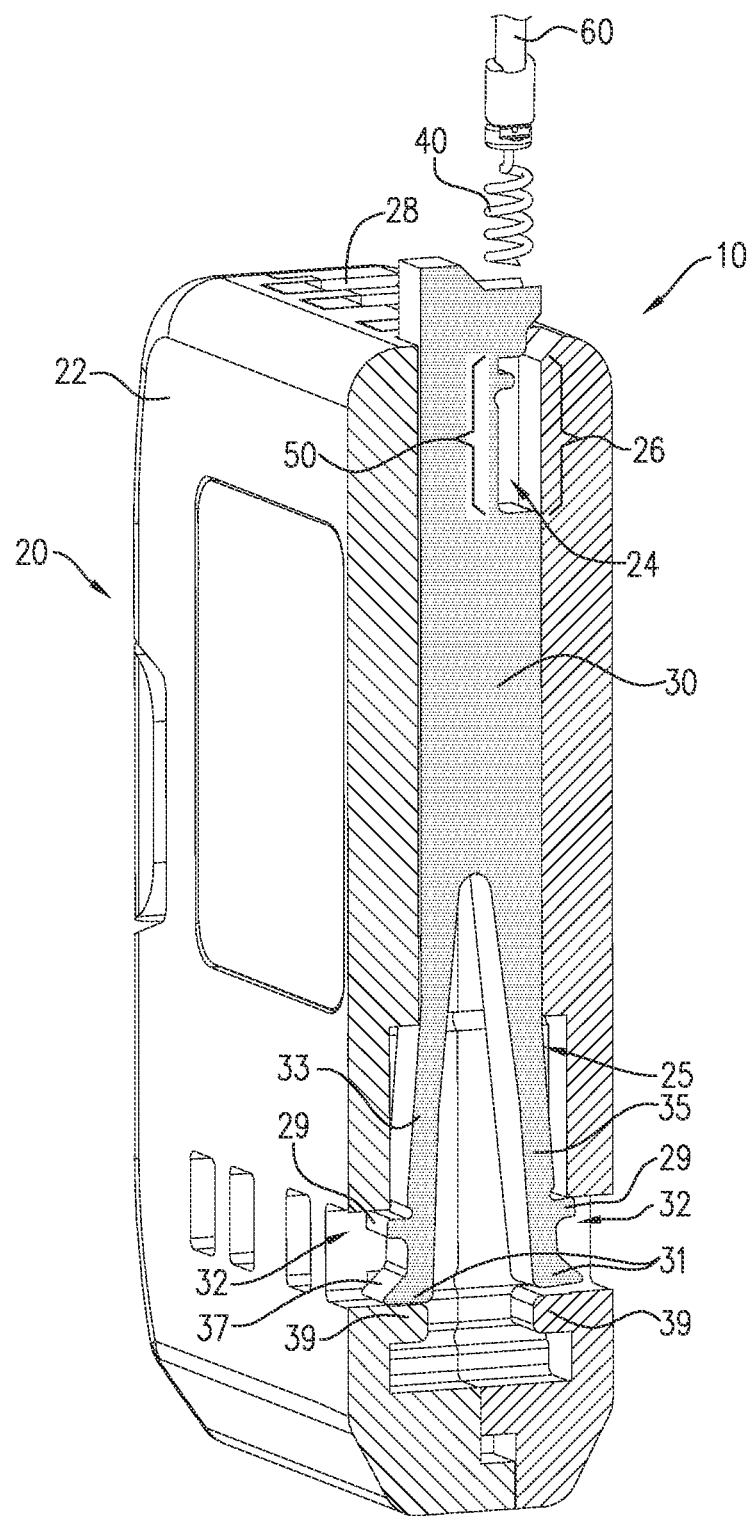

FIG. 3C shows anchor 40 being withdrawn proximally from zone 26 of channel 24 by the sufficient force or sufficient proximally-directed force being applied to the anchor by an anchor driver 60. In response to the sufficient force or sufficient proximally-directed force applied to the tissue anchor (i.e., if the force or proximally-directed force is greater than the pre-determined threshold force), the retaining member (e.g., pin 30) stops retaining the tissue anchor in zone 26. For example, and as shown in FIG. 3C, the sufficient force or sufficient proximally-directed force overcomes the retention provided by pin 30 and legs 33 and 35 of pin compress toward each other.

It is hypothesized that this configuring of device 20 to require that the sufficient force or sufficient proximally-directed force be applied to tissue anchor 40 prevents inadvertent movement and/or exit of the tissue anchor (e.g., due to general transport or handling of the device), and/or withdrawal of the anchor by driver when the driver is sub-optimally coupled to the anchor.

Following removal of anchor 40 from channel 24, a proximal portion of pin 30 remains exposed from opening 28. This may be particularly useful for a physician using a multiple-anchor-handling device, such as device 20, e.g., to prevent the physician inadvertently attempting to obtain an anchor from an empty zone 26. That is, the proximal portion of pin 30 functions as an empty-housing indicator.

Reference is now made to FIGS. 4A-B, 5A-B, and 6A-C, which are schematic illustrations of respective pins 30 shaped to define cradles 50 at proximal ends thereof for cradling and holding a respective tissue anchor 40, in accordance with some applications. As shown in FIGS. 4A-B, cradle 50 is shaped so as to define first and second slanted surfaces 51a and 51b. For some applications, slanted surfaces 51a and 51b adjoin to form an apex 52 of cradle 50. For some applications, a narrow horizontal surface connects the bottom edges of slanted surfaces 51a and 51b such that three surfaces of cradle 50 contact anchor 40. For some applications, a narrow curved, or semicircular, surface connects the bottom edges of slanted surfaces 51a and 51b such that three surfaces of cradle 50 contact anchor 40. For clarity of illustration, anchor 40 is not shown. Surfaces 51a and 51b are configured to abut against anchor 40 such that anchor 40 fits snugly in anchor-storage zone 26. As shown, first and second slanted surfaces 51a and 51b collectively form a generally "V"-shape in cross-section, as shown. For some applications, surfaces 51a and 51b are curved so that cradle 50 forms a semi-circular cross-section. In any embodiment, surface 51a and 51b are configured to contact as much surface area of anchor 40 as possible in order to support a longitudinal length of anchor 40 and prevent anchor 40 from translating. Since anchor 40 is typically rigid, surfaces 51a and 51b contact as much surface area of anchor 40 in order to distribute loading.

For some applications, surfaces 51a and 51b support only core 41 of anchor 40. For some applications, surfaces 51a and 51b support the entire anchor 40 including core 41 and tissue-engaging member 44.

FIGS. 5A-B show cradle 50 defining first and second straight surfaces 53a and 53b that are coupled to a flat base 55 such that three surfaces of cradle 50 contact anchor 40. For some applications, base 55 defines a narrow curved, or semicircular, surface connects the bottom edges of straight surfaces 53a and 53b such that three surfaces of cradle 50 contact anchor 40. For clarity of illustration, anchor 40 is not shown. Surfaces 53a and 53b and base 55 are configured to abut against anchor 40 such that anchor 40 fits snugly in anchor-storage zone 26. In any embodiment, surface 53a and 53b and base 55 are configured to contact as much surface area of anchor 40 as possible in order to support a longitudinal length of anchor 40 and prevent anchor 40 from translating. Since anchor 40 is typically rigid, surfaces 53a and 53b and base 55 contact as much surface area of anchor 40 in order to distribute loading.

For some applications, cradle 50 is shaped so as to define only base 55 and not surfaces 53a and 53b.

For some applications, surfaces 53a and 53b support only core 41 of anchor 40. For some applications, surfaces 53a and 53b support the entire anchor 40 including core 41 and tissue-engaging member 44.

Figure 6A:
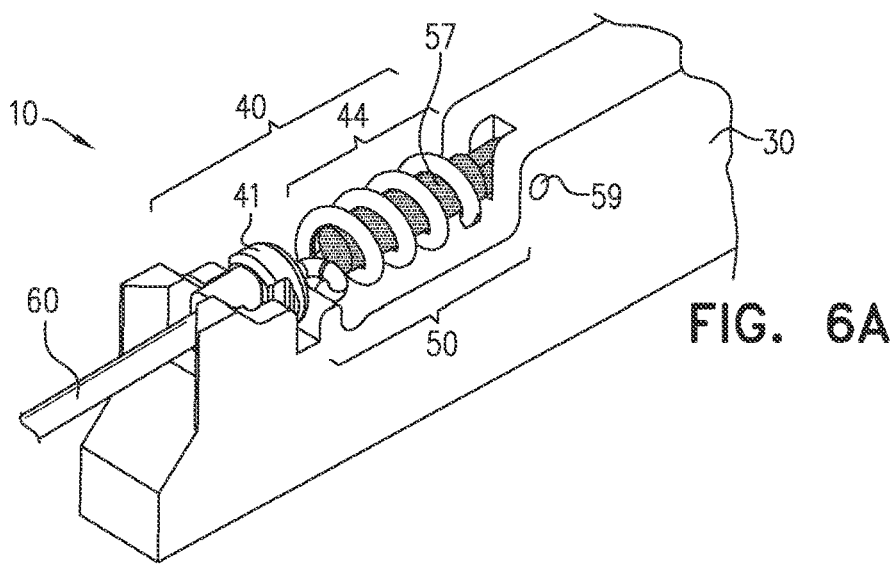
Figure 6B:
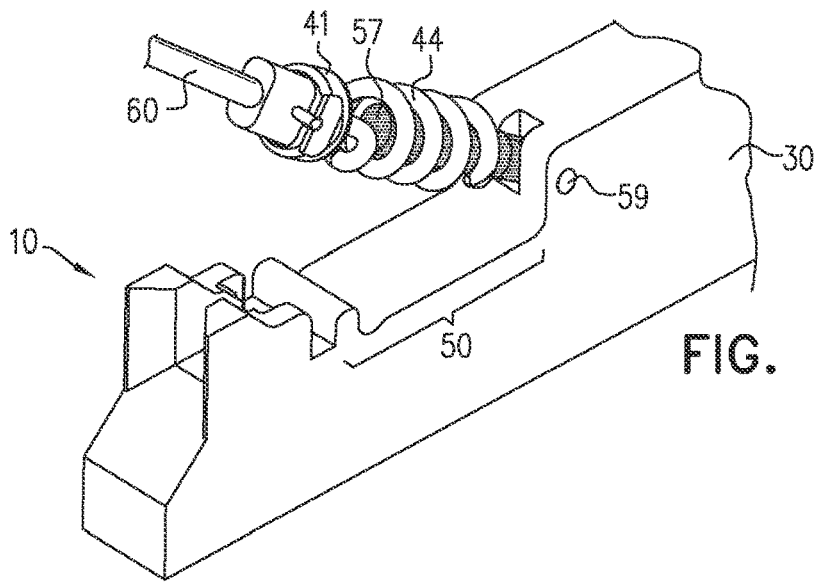
Figure 6C:
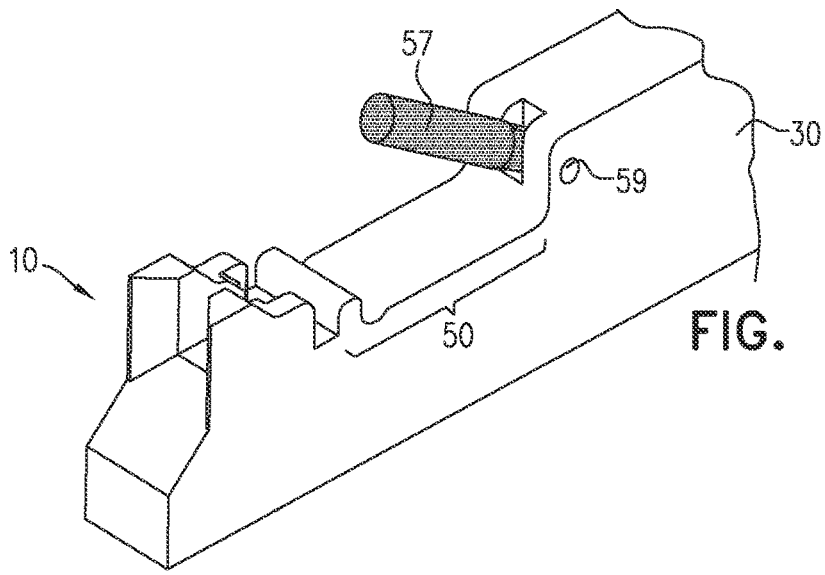

For either cradle 50 shown in FIGS. 4A-B and 5A-B, for some applications, cradle 50 comprises a pivoting support pillar 57, as shown in FIGS. 6A-C, which enables anchor 40 to pivot once cradle 50 of pin 30 emerges and is exposed from within anchor-storage zone 26 in response to proximal pulling of pin 30 at least partially from within channel 24. The pivoting pillar 57 can extend within tissue-engaging member 44 and enable anchor 40 to be articulated and pivot away from cradle 50. As shown, member 44 is shaped so as to define a helix, and pillar 57 is disposed within a lumen defined by the helix. Additionally, pillar 57 functions to provide support to tissue anchor 40 and to distribute loading. Pillar 57 is shaped so as to define a rod. For such applications, pin 30 is shaped so as to define a pivot pin 59, or a pivot, coupled to pivoting pillar 57 which enables the pivoting pillar to facilitate pivoting of tissue anchor 40 angularly away from cradle 50, e.g., angularly away from a longitudinal axis of the retaining member.

Reference is now made to FIGS. 3A-C, 4A-B, and 5A-B. In the applications shown, device 20 comprises an inhibitor, configured to configure the retaining member (e.g., pin 30) to (i) retain the tissue anchor in anchor-storage zone 26, and (ii) to stop retaining the tissue anchor in response to the sufficient force or sufficient proximally-directed force. The distal end portion of each pin 30 is shaped so as to define first and second legs 33 and 35. Each leg can comprise or define a respective at least one detent at a distal end portion thereof. For example, each leg 33 and 35 of pin 30 comprises portion 29 which functions as a detent, while anchor 40 is disposed within anchor-storage zone 26, is held by a spring mechanism within a cavity 32 (e.g., a notch) defined in chamber 25, and thereby serves as the inhibitor. Additionally, each leg 33 and 35 of pin 30 comprises or defines a second detent 31. For some applications at least a portion of the retaining member (e.g., pin 30) is resilient, and thereby provides the spring mechanism. It is to be noted, however, that the use of other spring mechanisms is also possible. Legs 33 and 35 also function as a spring mechanism as they are able to compress radially inwardly toward each other.

As shown in FIG. 3A, for each channel 24, housing 22 is shaped so as to define a respective male coupling 39 in a vicinity of cavity 32. As shown in FIG. 2, each lateral portion 22a and 22b of housing 22 is shaped so as to define a respective cavity 32 that is in fluid communication with channel 24 and/or chamber 25. During a retaining state of the retaining member (e.g., pin 30), pin 30 is configured to retain anchor 40 in anchor-storage zone 26. During the retaining state the detent, or portion 29, of each leg 33 and 35 is maintained within a respective cavity 32 of housing 22. Additionally, portion 29 and detent 31 of each leg 33 and 35 of pin 30 surround and hug male coupling 39. In such a manner, portion 29 functions as an inhibitor. The inhibitor provides resistance that (i) inhibits sliding of pin 30 through chamber 25, e.g., prevents sliding of the pin in the absence of a sufficient proximally-directed force (e.g., as shown in FIGS. 3A-B), and (ii) stops inhibiting the sliding in response to the sufficient proximally-directed force by detent 31 moving proximally away from male coupling 39 and into cavity 32 (e.g., as shown in FIG. 3C). For example, and as shown, a resilient portion (e.g., legs 33 and 35) deforms (e.g., bends or moves) in response to the sufficient proximally-directed force. In such a manner, legs 33 and 35 move toward each other. This can be facilitated by detents 31 of each leg 33 and 35 and male coupling 39. Since each detent 31 has a face 37 that is appropriately angled or slanted, the proximally-directed force is converted into lateral movement of detent 31 proximally around male coupling 39 and into cavity 32 as shown in FIG. 3C. For example, and as shown, detent 31 can have a beveled edge.

For such applications, once detent 31 has moved into cavity 32, a proximally-directed force that is smaller than the threshold force is sufficient to move pin 30 further proximally. That is, once the initial resistance provided by the inhibitor is overcome, anchor 40 is further withdrawable using a smaller force than that required to overcome the initial resistance.

(It will be understood by those skilled in the art that it is possible to use other configurations to achieve a behavior similar to that described above. For example, housing 22 can define a protrusion (e.g., a detent), and pin 30 can comprise a cavity (e.g., a notch) into which the protrusion extends.)

Due to slanted face 37 of detent 31, a distal force can be applied to push pin 30 back into the retaining state shown in FIGS. 3A-B. That is, once anchor 40 is removed form cradle 50, a new anchor 40 may be reloaded into cradle 50 of pin 30, and pin 30 may be pushed distally within channel 24 of housing 22 such that the newly-loaded anchor 40 is positioned within anchor-storage zone 26 of housing 22. That is, when a distally-directed force that is greater than a predetermined threshold force is applied to pin 30 and/or to a newly-loaded tissue anchor 40 into cradle 50, pin 30 is able to retain the new anchor 40.

For some applications, housing 22 defines a second cavity therein (not shown), disposed proximally to cavity 32. Once pin 30 is moved proximally, portion 29 engages with the second cavity, while detent 31 is disposed within cavity 32. For some applications, housing 22 is at least in part transparent, so as to enable viewing of the coupling of the anchor driver to anchor 40, and/or withdrawal of the anchor from the housing. For such applications, for each pin, housing 22 defines first, second, third, and fourth cavities. Portions 29 engaging with first and second cavities and detents 31 engaging with third and fourth cavities.

Reference is now made to FIGS. 7A-C, 8, 9, and 10A-B, which are schematic illustrations of a wearable article 100 coupled to a holder 90 shaped so as to define a space 92 for receiving anchor-handling device 20, in accordance with some applications. Holder 90 is shaped so as to define a housing, e.g., a receptacle, as shown, and a coupling 94 configured to reversibly couple anchor-handling device 20 to holder 90. Wearable article 100 is configured to temporarily affix anchor-handling device 20 to a body of an operating physician that is using anchor-handling device.

Holder 90 can be shaped so as to define two scaffolding lateral arms which create two openings at either end of holder 90. That is, even though device 20 is shown as entering and exiting one opening at a first end of holder 90 in FIGS. 7A-C, it is to be noted that device 20 can enter and exit the opposite opening at the other end of housing 90 as well. It is to be noted that, for some applications, one end of holder 90 can be closed while the opposite end is open (configuration not shown).

For some applications, wearable article 100 comprises an adhesive configured to temporarily affix anchor-handling device 20 to a garment of the operating physician. For some applications, wearable article 100 comprises an adhesive configured to temporarily affix anchor-handling device 20 to a glove of the operating physician. For some applications, wearable article 100 comprises a hook-and-loop fastener configured to temporarily affix anchor-handling device 20 to a garment of the operating physician. For some applications, wearable article 100 comprises hook-and-loop fastener configured to temporarily affix anchor-handling device 20 to a glove of the operating physician. It is to be noted that any suitable device for temporarily affixing anchor-handling device 20 to the physician, e.g., magnets, pins, etc., can be used.

For some applications, wearable article 100 comprises a thin metal sheet. For some applications, the thin metal sheet is malleable in order to confirm article 100 to a particular part of the body of the operating physician.

Reference is now made to FIGS. 8, 9, and 10A-B. For some applications, wearable article 100 comprises a band 102. For some applications, wearable article 100 comprises a wristband. In some implementations, band 102 is flexible. For some applications, band 102 comprises a stretchable material. For some applications, band 102 comprises a shape-memory material. For some applications, article 100, e.g., band 102, comprises a rigid material at at least a portion thereof in a vicinity of holder 90.

For some applications, band 102 comprises a closed loop and is stretchable to pass, or slide, over a hand of the operating physician such that the operating physician can wear device 20 on his/her wrist or around a part of the central region of the hand of the operating physician. For some applications, band 102 comprises a first portion comprising a stretchable and flexible material and a second portion comprising a material that is less stretchable and less flexible than the stretchable and flexible material of the first portion. For such applications, band 102 is variably stretchable and variably flexible. For such applications, the second portion can be in a vicinity of holder 90. For some applications, the more-flexible and more-stretchable section of band 102 are disposed at lateral sections of the band, e.g., not in a vicinity of holder 90.

Figure 10A:
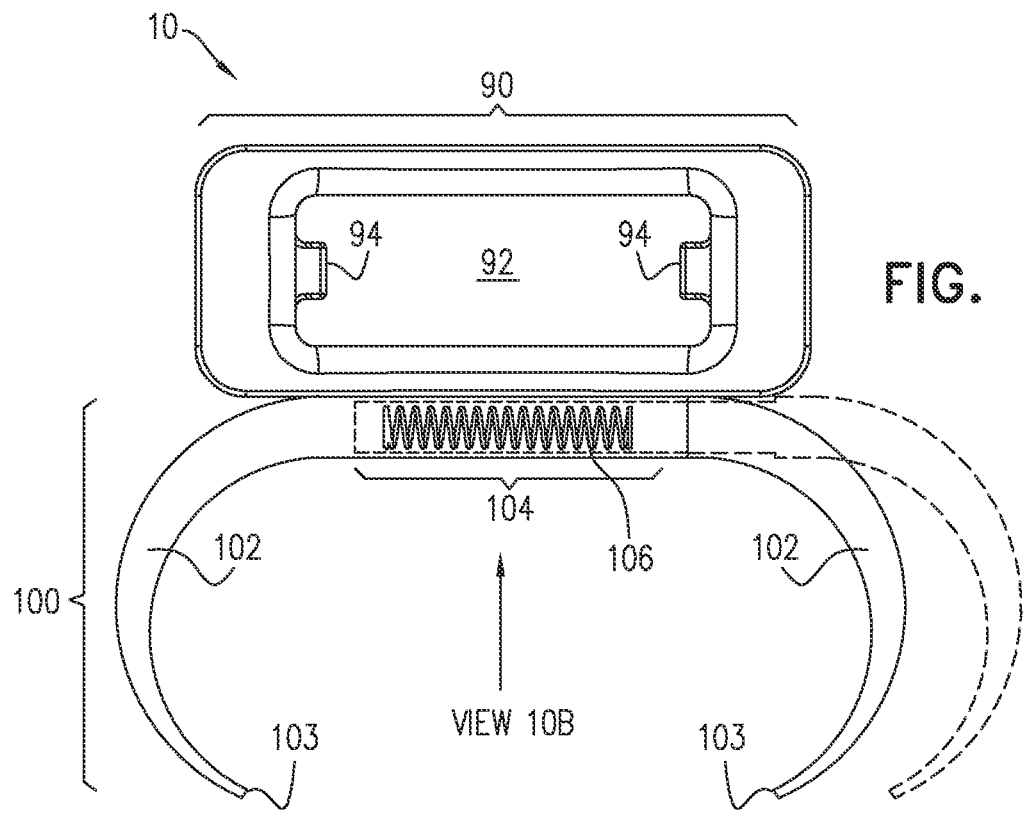
Figure 10B:
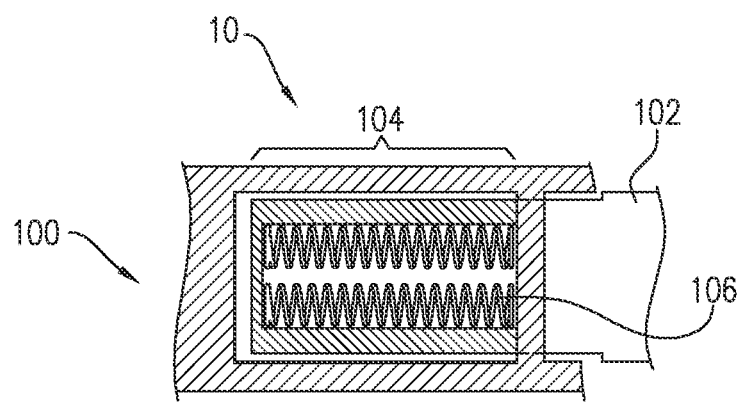

As shown in FIG. 10A, band 102 comprises first and second ends 103. For some applications, first and second ends 103 are separable, e.g., by separating first and second portions, e.g., halves, of band 102 using an adjustment mechanism 104 coupled to wearable article 100 in a vicinity of holder 90. Adjustment mechanism 104 comprises a spring-loaded coupling 106 that enables the two portions of band 102 to be expanded and moved apart from each other. Due to the presence of spring-loaded coupling 106, the portions of band 102 have a tendency to close toward each other to facilitate contract band 102 and facilitate a snug coupling of device 20 to the operating physician. Details of spring-loaded coupling 106 are shown in FIG. 10B.

Figure 8:
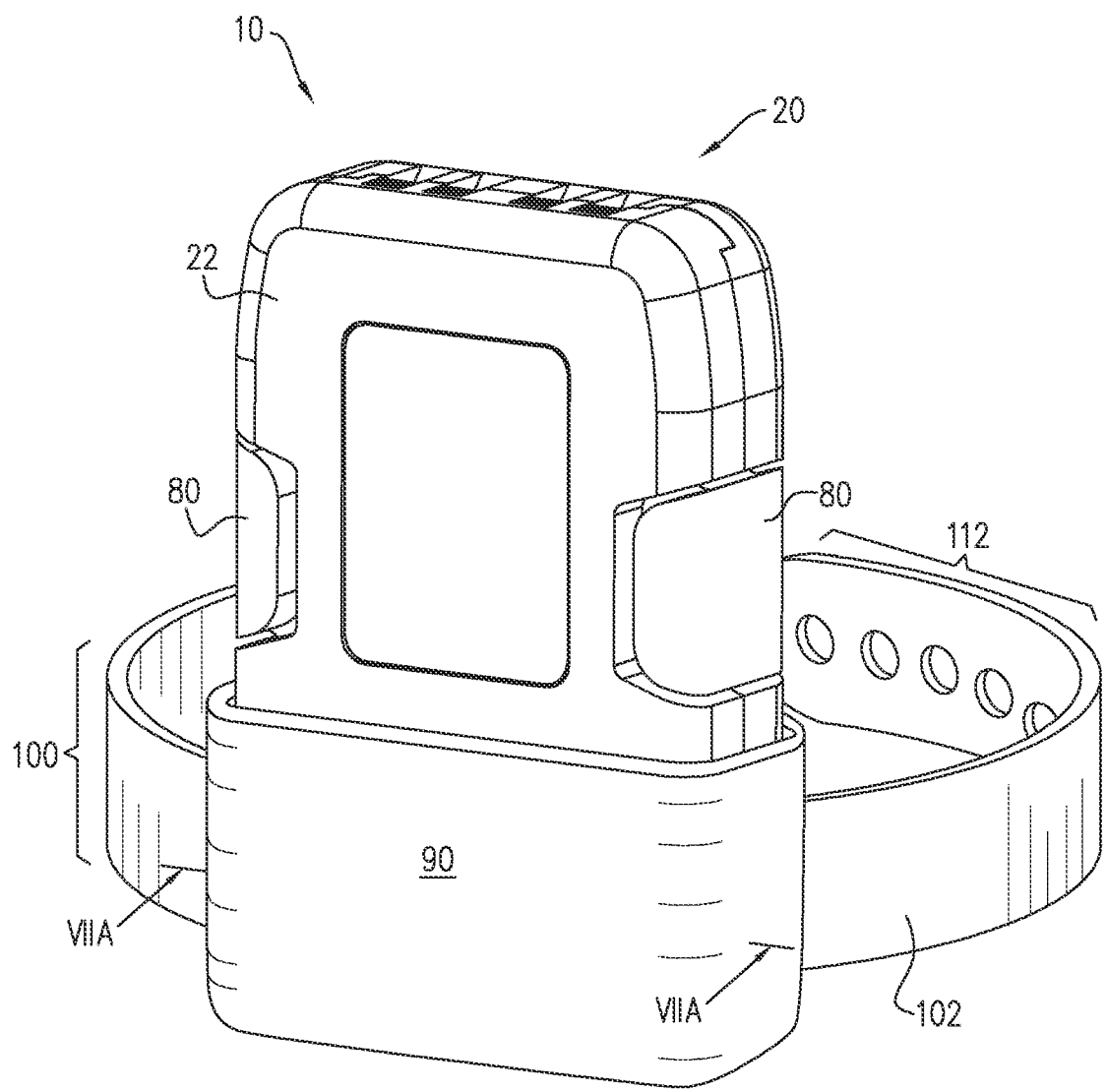

As shown in FIG. 8, band 102 is adjustable using a clasp 112. As shown in FIG. 8, clasp 112 is shaped so as to define a plurality of openings on one portion of band 102, while band 102 is shaped so as to define a coupling (not shown) on an opposing portion of band 102 which engages any one of the openings of clasp 112. For some applications, clasp 112 comprises a magnet and magnetically clasps the end portions of band 102. For either embodiment, the size of band 102 is adjustable.

For some applications, system 10 comprises a design in which a single band 102 is wrappable around both the wrist and the central region of the hand of the operating physician. For some applications, system 10 comprises a multi-band design in which two or more bands are used to wrap around the wrist and the central region of the hand of the operating physician. In either embodiment, the multiple wrapping or multi-band design imparts more stability during use of device 20.

Reference is now made to FIGS. 8, 9, and 10A-B. For some applications, band 102 comprises an adhesive in order to prevent movement or sliding of wearable article 100 with respect to the body of the operating physician.

Reference is now made to FIGS. 7A-C and 10A-B. Holder 90 is shaped so as to define a space 92 for receiving anchor-handling device 20 and comprises a coupling 94 configured to reversibly couple device 20 to holder 90 and thereby to wearable article 100. In some implementations, coupling 94 comprises a male coupling that protrudes into space 92. For some applications, coupling 94 is rigid. For some applications, coupling 94 comprises a detent which is moveable with respect to walls of holder 90 in response to force applied thereto, e.g., by housing 22 of device 20.

Device 20 is shaped so as to define a female coupling 84, e.g., a cavity, shaped so as to receive male coupling 94 of holder 90 in order to facilitate reversible locking of anchor-handling device 20 to holder 90.

Anchor-handling device 20 comprises a detent 82 which is movable responsively to force applied thereto by male coupling 94 of holder 90 in order to facilitate reversible locking of anchor-handling device 20 to holder 90. As shown in FIG. 7A, detent 82 is disposed in its resting and locking position, distally to male coupling 94 in order to lock in place device 20. Anchor-handling device 20 comprises a depressible element 80 coupled to detent 82. As shown, device 20 is shaped so as to define a respective detent 82 and depressible element 80 at either lateral side of housing 22. As shown in FIG. 7B, depressible element 80 is pushable by the operating physician in order to apply an inward force to detent 82 so that detent 82 clears male coupling 94 of holder 90. Once detent 82 is not engaged with male coupling 94 of holder 90, device 20 can be moved proximally away from holder 90 so that device 20 is decoupled from holder 90, as shown in FIG. 7C. At this point, force is not applied to depressible element 80, and detent returns to its resting position.

Device 20 is then recouplable to holder 90. For some applications, depressible elements 80 are pushed inward in order to move detents inwardly to clear male couplings 94 as device 20 is moved distally into space 92 of holder 90. For some applications, detents are moved responsively to distal movement of housing 22 of device 20 against male couplings 94 of holder 90.

Reference is again made to FIGS. 8, 9, and 10A-B. For some applications, an articulatable coupling, e.g., a swivel coupling, couples holder 90 to wearable article 100 in a manner in which the holder is articulatable, e.g., swivelable, relative to the wearable article. For some applications, a first portion of wearable article 100 is more rigid than a second portion of wearable article 100. For such applications, the second portion of wearable article 100 imparts flexibility and stretchability to article 100.

Figure 9:
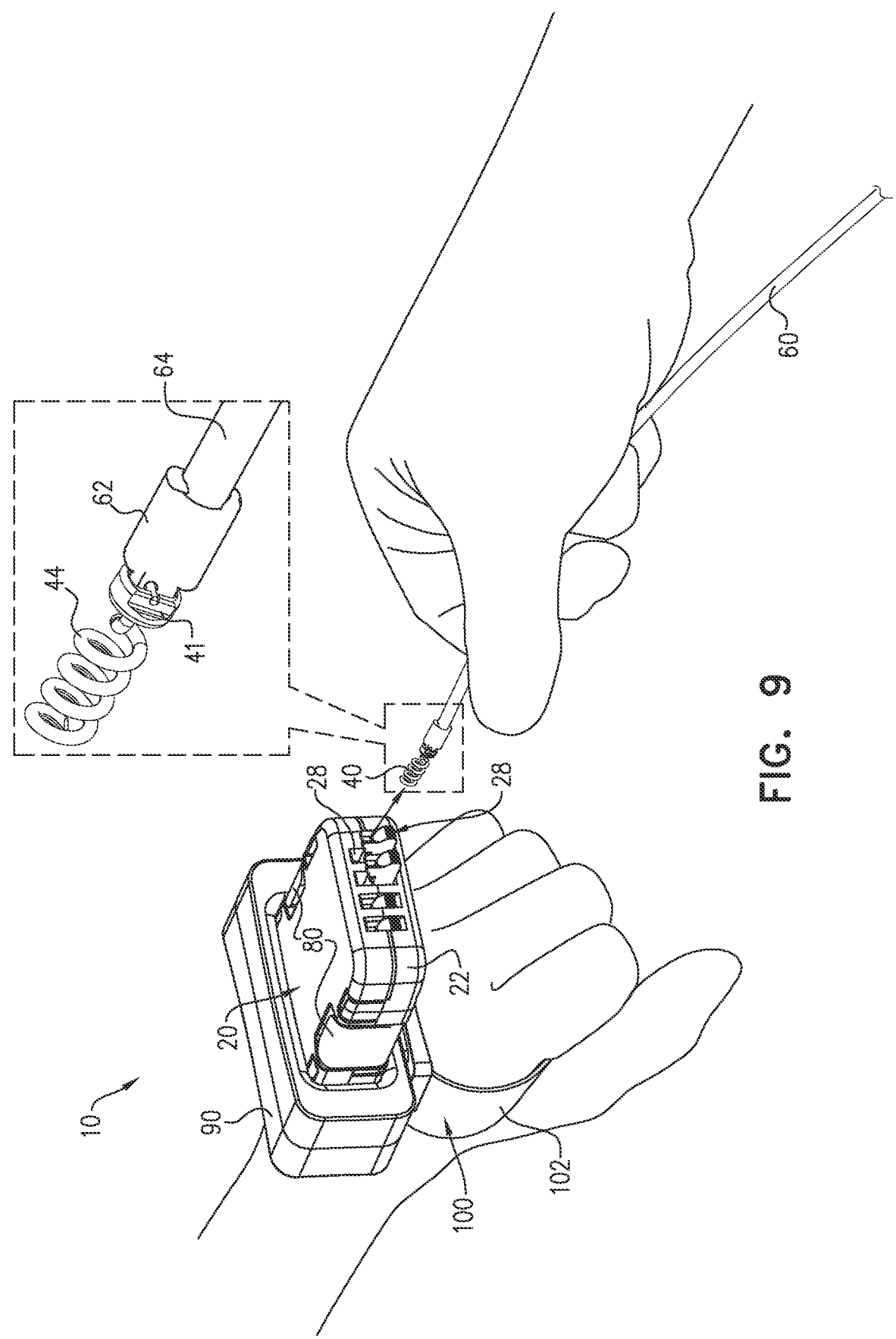

FIG. 9 shows anchor 40 having been fully withdrawn out of channel 24 via opening 28. Anchor driver 60 is brought toward holder 90 and wearable article 100, e.g., band 102 as shown, in order to engage driver 60 with an anchor disposed within device 20. Driver 60 withdraws an anchor 40, as described hereinabove. Once anchor 40 has been fully withdrawn, driver 60 can be used to anchor tissue anchor 40 to tissue of a subject, e.g., by driving tissue-engaging member 44 of the anchor into the tissue.

Various tissue anchors as may be known in the art can be used.

In some implementations, using driver 60, anchor 40 can be advanced through a transluminal implant-delivery system and used to couple an implant, e.g., an annuloplasty structure, to tissue of a subject.

In some implementations, driver 60 comprises an anchor-engaging head 62 at a distal end of the driver, and an elongate advanceable element 64 proximal to the anchor-engaging head. For some applications, elongate advanceable element 64 comprises a tube shaped to define a lumen. For some applications, elongate advanceable element 64 comprises a shaft. Elongate advanceable element 64 is flexible and advanceable (e.g., transcatheterally) through vasculature of a subject, and can have a length greater than 20 cm, and/or less than 2.5 m, such as greater than 50 cm and/or less than 1.5 m, e.g., between 0.9 m and 1.2 m. For some applications, driver 60 comprises a handle (now shown) at a proximal end of elongate advanceable element 64, the handle comprises an adjuster (e.g., a switch or a lever) configured to actuate engaging head 62.

FIG. 9 shows anchor 40 having been fully removed from the housing. For some applications, to facilitate full disengagement of anchor 40 from pin 30, the anchor is moved slightly laterally with respect to pin 30. For some applications, pin 30 comprises pivoting pillar 57, as described hereinabove with reference to FIGS. 6A-C. Once anchor 40 has been fully withdrawn, driver 60 can be used to anchor tissue anchor 40 to tissue of a subject.

As shown in FIG. 9, two anchors 40 have been removed from device 20. Following the removal of anchors 40, the proximal portions of respective pins 30 protrude out of respective openings 28 and function as indicators as to how many anchors have been removed from device 20. For some applications, new anchors can be reloaded into device by placing them within the cradles of pins 30 that are exposed from within housing 22 of device 20.

Figure 11A:
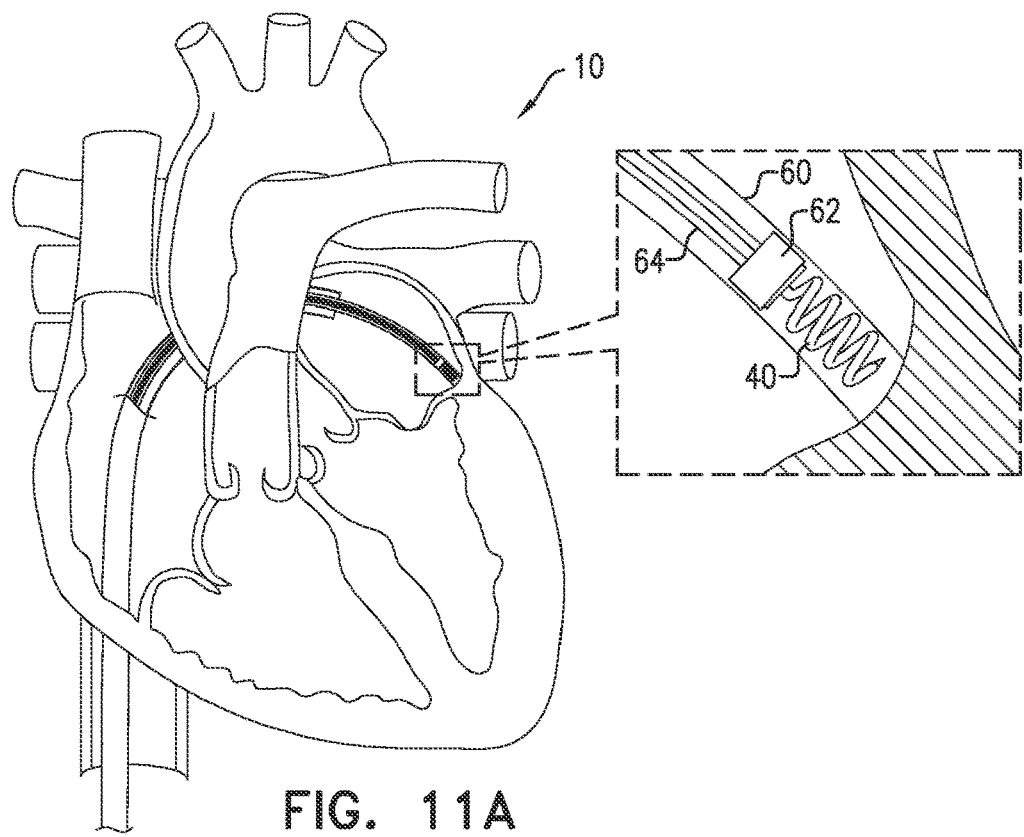
FIGS. 11A-B are schematic illustrations of an example of an elongate advanceable element of an anchor driver reinforced by a shaft, in accordance with some applications.
Figure 11B:
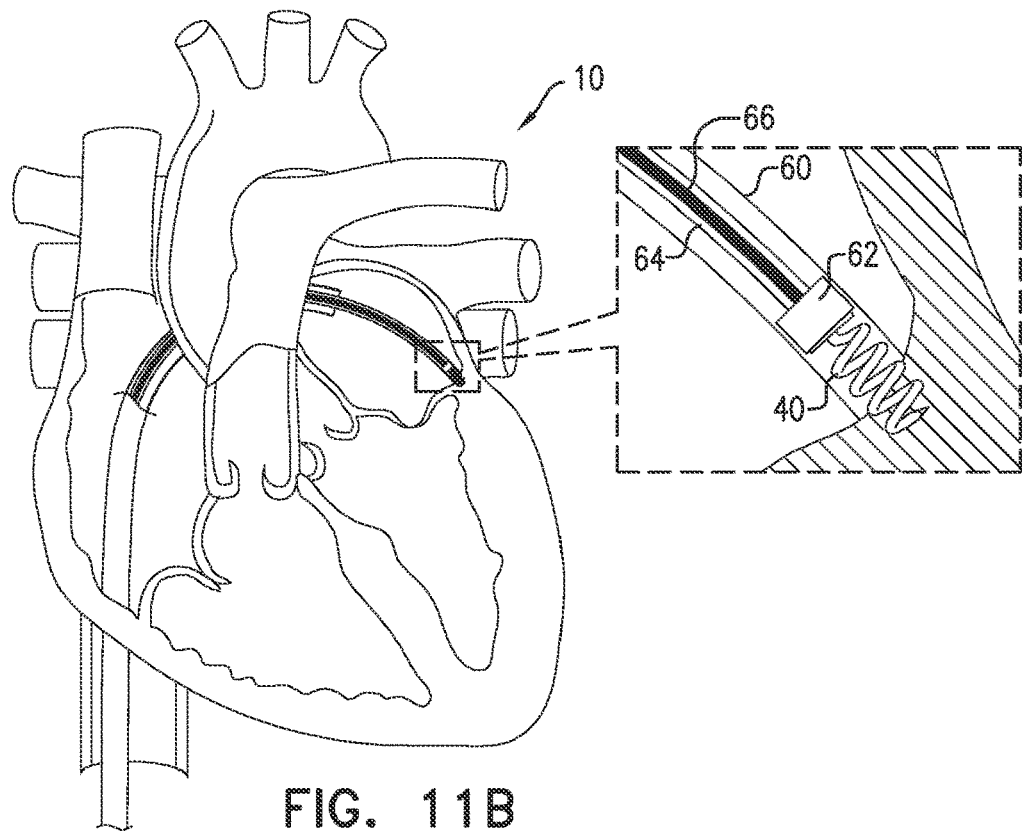

Reference is now made to FIGS. 11A-B, which are schematic illustrations of anchor driver 60 being advanced through vasculature of a patient, in accordance with some applications. Anchor driver comprises elongate advanceable element 64. For such applications, elongate advanceable element 64 can comprise a flexible, elongate tube. A distal end of element 64 is coupled to anchor-engaging head 62. A shaft 66 is advanceable through the lumen of the tube of element 64. In some implementations, shaft 66 is more rigid than element 64.

Shaft 66 is slidable proximally and distally with respect to the tube of element 64. When a distal end portion of element 64 is devoid of shaft 66 (as shown in FIG. 11A), the distal end portion of element 64, and thereby, a distal portion of anchor driver 60, is more flexible and less stiff and can enable more range of motion of anchor-engaging head 62. When a distal end portion of element 64 is devoid of shaft 66, anchor driver 60 (or at least the distal end portion of element 64) is in a more flexible state.

Once the operating physician advances shaft 66 within the distal portion of the tube of element 64, the distal end portion of element 64 is less flexible and stiffer. The presence of shaft 66 within the lumen of the tube of element 64 (as shown in FIG. 11B) reduces the ability for the tube of element 64 to bend. When a portion of shaft 66 is within the lumen of the distal end portion of element 64, anchor driver 60 (or at least the distal end portion of element 64) is in a less flexible state.

Increased flexibility of element 64 is useful during navigating anchor driver 60 through vasculature and steering the distal end portion of anchor driver 60 to the appropriate location along tissue of the annulus of a valve. Therefore, during these steps, shaft 66 is not present within the lumen of element 64, as shown in FIG. 11A. During these steps, the distal end of elongate advanceable element 64 and the distal end portion of anchor driver 60 are in a first flexible state (as shown in FIG. 11A).

In some applications, shaft 66 is positioned within the lumen of element 64 during connecting of anchor driver 60 to an anchor within anchor-handling device 20 as described hereinabove, and during rotating of element 64 and applying torque to element 64 in order to apply torque to anchor 40 during insertion into tissue (e.g., driving anchor 40 into tissue) and retrieval of anchor 40 from tissue. During these steps, the distal end of elongate advanceable element 64 and the distal end portion of anchor driver 60 are in a second flexible state that is less flexible than the first flexible state (as shown in FIG. 11B). In the second flexible state, the distal end portion of element 64 and the distal end portion of anchor driver 60 are more rigid.

As such, movement of shaft 66 longitudinally proximally and distally with respect to element 64 facilitates transitioning of the distal end of elongate advanceable element 64 between the first and second flexible states.

As shown in FIG. 11A, when element 64 is devoid of shaft 66, pivoting, tilting, movement, bending, flexing, or articulating the distal end portion of element 64 is increased and the distal end portion of elongate advanceable element 64 and the distal end portion of anchor driver 60 assume a more flexible state. That is, pivoting, tilting, movement, bending, flexing, or articulating of head 62 with respect to the distal end portion of elongate element 64 is allowed.

For some applications, anchor driver 60 is assembled such that shaft 66 is disposed within the lumen of element 64 (as shown in FIG. 11B). During coupling of anchor driver 60 to tissue anchor 40, e.g., as described hereinabove with reference to FIGS. 1-6C, it is advantageous for driver 60 to be in the less flexible state as shown in FIG. 11B. Anchor driver 60 is then transitioned to the more flexible state (shown in FIG. 11A) by retracting shaft 66 from at least the distal end portion of elongate advanceable element 64. In this state, anchor driver 60 is more flexible. This more flexible state of anchor driver 60 (shown in FIG. 11A) is advantageous during navigating anchor driver 60 through vasculature and steering the distal end portion of anchor driver 60 to the appropriate location along tissue of the annulus of a valve. Once anchor driver 60 has delivered anchor 40 to the appropriate location of tissue, anchor driver 60 is transitioned to the less flexible state (shown in FIG. 11B) by advancing shaft 66 within the distal end portion of element 64, in order to impart rigidity to anchor driver 60 as torque is applied to elongate advanceable element 64 so as to apply torque to anchor 40 in order to drive anchor 40 into tissue. Transitioning of anchor driver 60 between the more and less flexible states is facilitated by distal and proximal sliding of shaft 66 within the lumen of element 64.

As shown in FIG. 11B, when shaft 66 is disposed within the lumen of the distal end portion of elongate advanceable element 64, the distal end portion of anchor driver 60 assume the less flexible state. That is, pivoting, tilting, movement, bending, flexing, or articulating of head 62 with respect to the distal end portion of elongate element 64 is limited, restricted, or, in some cases, prevented.

During disengaging of anchor-engaging head 62 from tissue anchor 40, shaft 66 is retracted as to transition anchor driver 60 into the more flexible state and implant more flexibility to the distal end of anchor driver 60 during the flexing and bending of element 64 with respect to tissue anchor 40, now implanted.

Reference is now made to FIGS. 12, 13A-C, and 14A-B, which are schematic illustrations of an example anchor-engaging head 62 articulating with respect to elongate advanceable element 64, in accordance with some applications. Various anchor driver designs and various anchor-engaging head designs are possible. In some applications, a distal end of elongate advanceable element 64 is coupled to at least one coupling pin 162, e.g., a plurality of coupling pins 162, as shown. Anchor-engaging head 62 can be shaped so as to define at least one slotted opening 160 (e.g., a plurality, as shown), and coupling pin 162 and slotted opening 160 are moveable with respect to each other in order to facilitate articulating between anchor-engaging head 62 and elongate advanceable element 64.

Each slotted opening 160 can be shaped so as to circumferentially a main section 166 and at least one circumferentially extreme section 164. As shown, each opening 160 is shaped so as to define a respective extreme section 164 at either side of main section 166. For some applications, opening 160 can define a single extreme section 164. Main section 166 is longitudinally wider than each extreme section 164. For example, in some implementations, main section 166 is 1.5-2 times wider than a width of each extreme section 164. That is, a width of section 166 measured along a longitudinal axis 165 of the distal end portion of elongate advanceable element 64 is greater than a width of section 164 measured along axis 165. Opening 160 can be diamond-shaped or another shape.

Reference is now made to FIGS. 13A-C. Elongate advanceable element 64 is shown as being rotatable about longitudinal axis 165 of the distal end portion of elongate advanceable element 64 with respect to anchor-engaging head 62 so as to transition coupling pin 162 between main section 166 and extreme sections 164.

As shown in FIGS. 13A-B, when coupling pin 162 is disposed within main section 166, movement of anchor-engaging head 62 and elongate advanceable element 64 with respect to each other is facilitated and the distal end portion of elongate advanceable element 64 and the distal end portion of anchor driver 60 assume a more flexible state. That is, pivoting, tilting, movement, bending, flexing, or articulating of head 62 with respect to the distal end portion of elongate element 64 is allowed.

For some applications, anchor driver 60 is assembled such that pin 162 is disposed within extreme section 164 (as shown in FIG. 13C). During coupling of anchor driver 60 to tissue anchor 40, e.g., as described hereinabove with reference to FIGS. 1-6C, it is advantageous for driver 60 to be in the less flexible state as shown in FIG. 13C. Anchor driver 60 is then transitioned to the more flexible state (shown in FIGS. 13A-B) by rotating elongate advanceable element 64 with respect to anchor-engaging head 62, and by the rotating, moving coupling pin 162 from extreme section 164 to main section 166. In this state, anchor driver 60 is more flexible. This more flexible state of anchor driver 60 (shown in FIGS. 13A-B) is advantageous during navigating anchor driver 60 through vasculature and steering the distal end portion of anchor driver 60 to the appropriate location along tissue of the annulus of a valve. Once anchor driver 60 has delivered anchor 40 to the appropriate location of tissue, anchor driver 60 is transitioned to the less flexible state (shown in FIG. 13C) by rotating element 64 so as to move pin 162 into extreme section 164, in order to impart rigidity to anchor driver 60 as torque is applied to elongate advanceable element 64 so as to apply torque to anchor 40 in order to drive anchor 40 into tissue. Transitioning of anchor driver 60 between the more and less flexible states is facilitated by rotation of element 64 with respect to head 62 and thereby effecting movement of pin 162 between sections 164 and 166 of opening 160.

As shown in FIG. 13C, when coupling pin 162 is disposed within extreme section 164, movement of anchor-engaging head 62 and elongate advanceable element 64 with respect to each other is restricted and the distal end portion of elongate advanceable element 64 and the distal end portion of anchor driver 60 assume the less flexible state. That is, pivoting, tilting, movement, bending, flexing, or articulating of head 62 with respect to the distal end portion of elongate element 64 is limited, restricted, or, in some cases, prevented. Moving coupling pin 162 from main section 166 to extreme section 164 comprises locking anchor-engaging head 62 with respect to the distal end portion of elongate advanceable element 64.

When anchor driver 60 engages an anchor, e.g., from within device 20 as described hereinabove, coupling pin 162 is moved back into main section 166 so as to transition anchor driver 60 into the more flexible state and implant more flexibility to the distal end of anchor driver 60.

During disengaging of anchor-engaging head 62 from tissue anchor 40, coupling pin 162 is moved back into main section 166 so as to transition anchor driver 60 into the more flexible state and implant more flexibility to the distal end of anchor driver 60 during the flexing and bending of element 64 with respect to tissue anchor 40, now implanted.

Figure 14A:
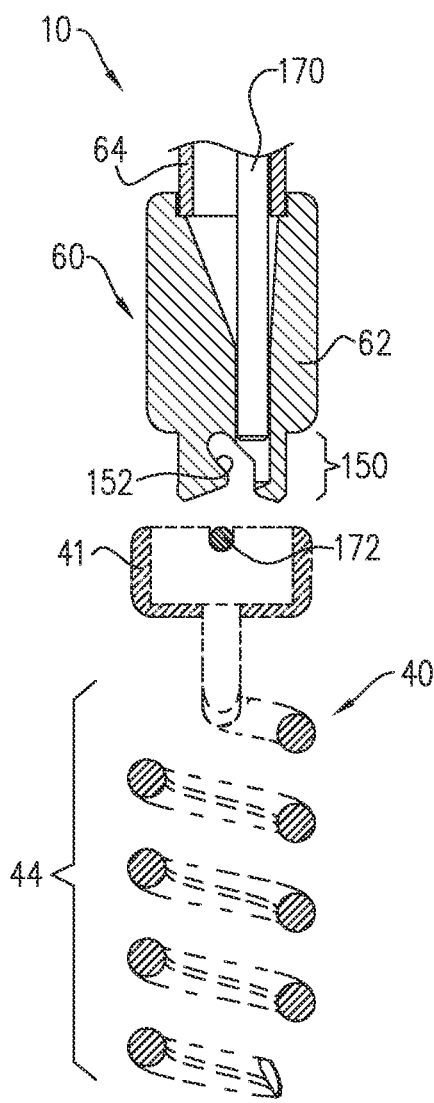
Figure 14B:
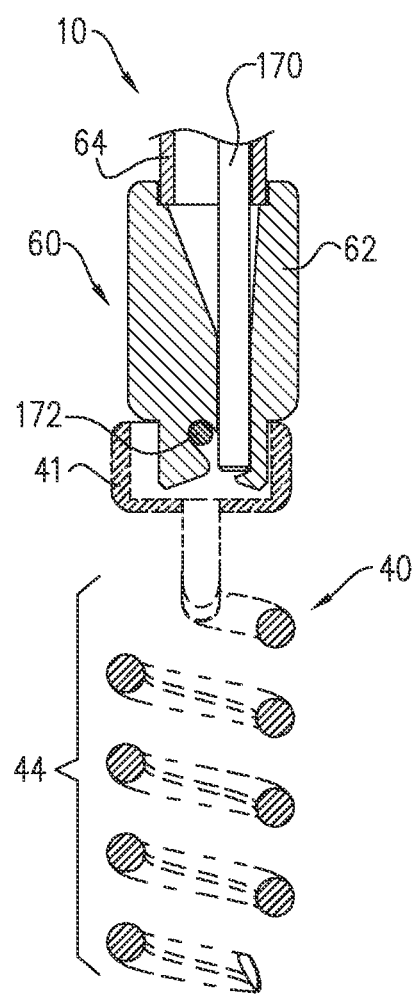

Reference is now made to FIGS. 14A-B, which are schematic illustrations of an example of an anchor-engaging head 62 and an anchor-retaining rod 170, in accordance with some applications. Rod 170 is slidable within a lumen of elongate advanceable element 64 so as to strengthen coupling between anchor-engaging head 62 and tissue anchor 40. Tissue anchor 40 is shaped so as to define a coupling member 172 at a proximal end of tissue anchor 40.

Figure 12:
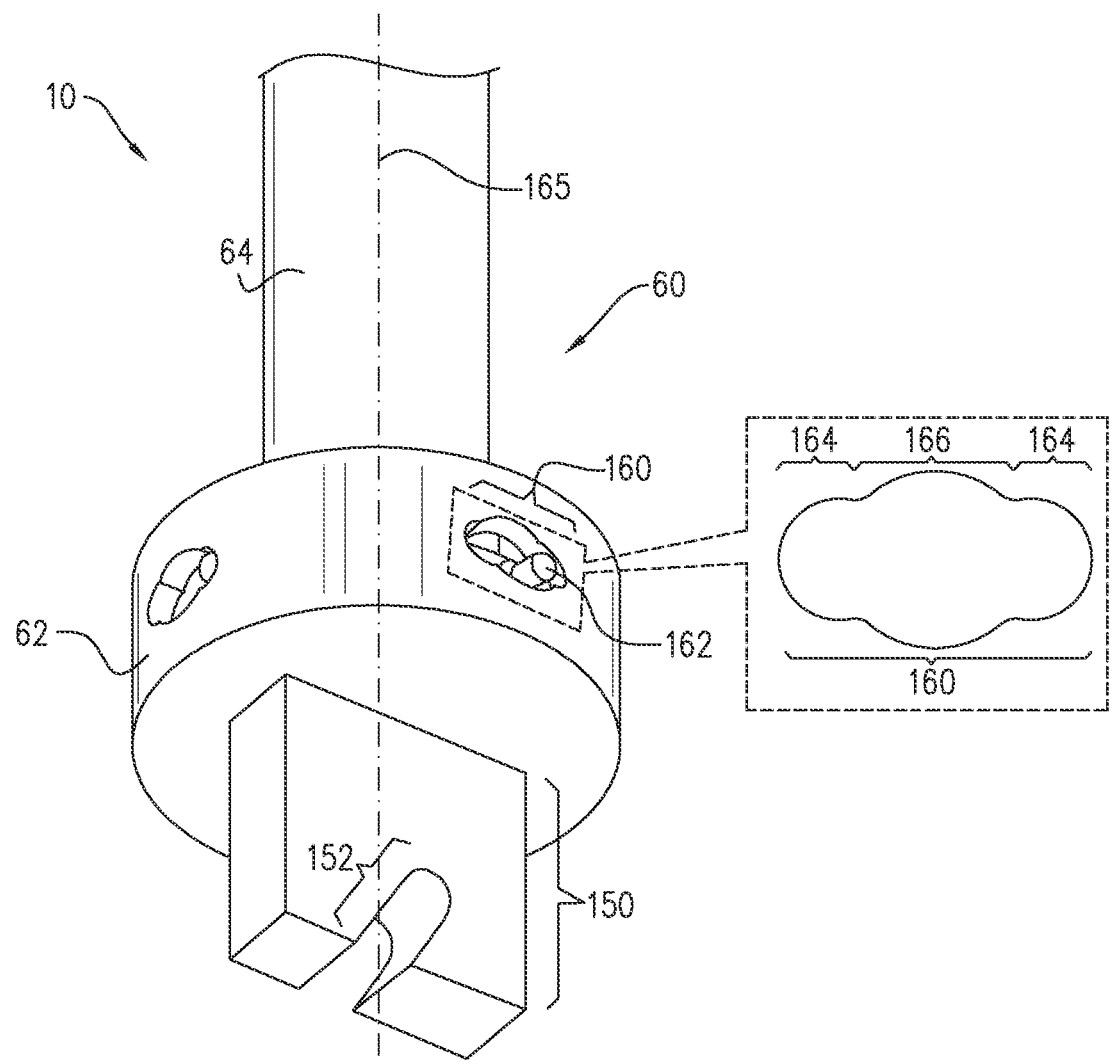

Reference is now made to FIGS. 12 and 14A-B. In some applications, as shown, anchor-engaging head 62 is shaped so as to define a protrusion 150 which is shaped so as to fit within a space defined by core 41 of tissue anchor 40. Protrusion 150 is shaped so as to define a slot 152 for receiving a coupling member 172 of tissue anchor 40. Anchor-engaging head 62 has a longitudinal axis, i.e., axis 165 of the distal end portion of elongate advanceable element 64, and wherein slot 152 is angled at a nonzero angle with respect to the longitudinal axis. Anchor driver 60 is pivoted in order to engage head 62 with coupling member 172 of anchor 40.

As shown in FIG. 14A, prior to the engaging of head 62 with anchor 40, a distal end of rod 170 can be disposed proximally to slot 152. Once engaging head 62 pivots to slide coupling member 172 within slot 152, rod 170 can be slid distally so that the distal end of rod 170 slides within a portion of slot 152 in order to reinforce the coupling between anchor-engaging head 62 and tissue anchor 40 (FIG. 14B). Rod 170 also can help reinforce the coupling during attachment and insertion (e.g., corkscrewing, etc.) of anchor 40 into tissue. The distal end of rod 170 partially obstructs slot 152 so as to restrict decoupling of anchor 40 from head 62.

Once tissue anchor 40 has been inserted into tissue, head 62 can be disengaged from anchor 40 by pulling proximally on rod 170 such that the distal end of rod 170 is disposed proximally to slot 152. Head 62 can then be pivoted and slid proximally so that slot 152 slide proximally away from coupling member 172.

Other designs of tissue anchors and anchor drivers and mechanisms for attachment and release therebetween are also possible.

Reference is now made to FIGS. 1-14B. For some applications, device 20 is used in combination with one or more techniques described in one or more of the following references, which are all incorporated herein by reference:

U.S. patent application Ser. No. 12/437,103 to Zipory et al., filed May 7, 2009, which published as US 2010/0286767. For example, (1) device 20 of the present application can be used to facilitate the techniques described with reference to FIGS. 2-3 and/or 6A-12 of US 2010/0286767 to Zipory et al., mutatis mutandis; (2) anchor driver 60 of the present application can comprise or correspond to anchor driver 68 and/or anchor deployment manipulator 24 of US 2010/0286767 to Zipory et al., mutatis mutandis; (3) tissue anchor 40 of the present application can comprise or correspond to anchor 38 of US 2010/0286767 to Zipory et al., mutatis mutandis; and/or (4) implant 140 of the present application can comprise or correspond to annuloplasty ring 22 of US 2010/0286767 to Zipory et al., mutatis mutandis.

U.S. patent application Ser. No. 12/689,635 to Zipory et al., filed Jan. 19, 2010, which published as US 2010/0280604. For example, (1) device 20 of the present application can be used to facilitate the techniques described with reference to FIGS. 2-3 and/or 11A-17 of US 2010/0280604 to Zipory et al., mutatis mutandis; (2) anchor driver 60 of the present application can comprise or correspond to anchor driver 68 and/or anchor deployment manipulator 24 of US 2010/0280604 to Zipory et al., mutatis mutandis; (3) tissue anchor 40 of the present application can comprise or correspond to anchor 38 of US 2010/0280604 to Zipory et al., mutatis mutandis; and/or (4) implant 140 of the present application can comprise or correspond to annuloplasty ring 22 of US 2010/0280604 to Zipory et al., mutatis mutandis.

PCT patent application IL2012/050451 to Sheps et al., filed Nov. 8, 2013, which published as WO 2013/069019. For example, (1) device 20 of the present application can be used to facilitate the techniques described with reference to FIGS. 14A-I of WO 2013/069019 to Sheps et al., mutatis mutandis; (2) system 120 of the present application can comprise or correspond to system 10 of WO 2013/069019 to Sheps et al., mutatis mutandis; (3) anchor driver 60 of the present application can comprise or correspond to anchor deployment manipulator 61 and/or anchor driver 36 of WO 2013/069019 to Sheps et al., mutatis mutandis; and/or (4) implant 140 of the present application can comprise or correspond to annuloplasty structure 222 and/or sleeve 26 of WO 2013/069019 to Sheps et al., mutatis mutandis.

PCT patent application IL2013/050860 to Sheps et al., titled "Controlled steering functionality for implant-delivery tool", filed on Oct. 23, 2013, which published as WO 2014/064694. For example, (1) device 20 of the present application can be used to facilitate techniques described with reference to FIGS. 10A-I, 12A-14B, 18A-C, 21-28, 34, and 36 of this PCT application titled "Controlled steering functionality for implant-delivery tool", mutatis mutandis; (2) system 120 of the present application can comprise or correspond to system 10 of this PCT application titled "Controlled steering functionality for implant-delivery tool", mutatis mutandis; anchor driver 60 of the present application can comprise or correspond to anchor deployment manipulator 61, anchor driver 36 and/or anchor driver 2338 of this PCT application titled "Controlled steering functionality for implant-delivery tool", mutatis mutandis; and/or (4) implant 140 of the present application can comprise or correspond to annuloplasty structure 222 and/or sleeve 26 of this PCT application titled "Controlled steering functionality for implant-delivery tool", mutatis mutandis.

PCT patent application IL2013/050861 to Herman et al., titled "Percutaneous tissue anchor techniques", filed on Oct. 23, 2013, which published as WO 2014/064695. For example, (1) device 20 of the present application can be used to facilitate the techniques described with reference to FIGS. 9A-C and/or 13A-D of this PCT application titled "Percutaneous tissue anchor techniques", mutatis mutandis; (2) tissue anchor 40 of the present application can comprise or correspond to tissue anchor 40 of this PCT application titled "Percutaneous tissue anchor techniques", mutatis mutandis; and/or (3) anchor driver 60 of the present application can comprise or correspond to anchor driver 500, anchor driver 236, deployment manipulator 261, or tool 80 of this PCT application titled "Percutaneous tissue anchor techniques", mutatis mutandis.

Reference is made to FIGS. 1-14B. In some implementations, the anchors are provided sterile within the anchor-handling device. As described hereinabove, for some applications, the anchor-handling device is configured such that returning the exposed portion of the retaining member back into the housing requires a distally-directed force that is more than twice as great (in the opposite direction) as the threshold force that was previously required to move the portion out of the housing. For example, the moving of the portion back into the housing may be in effect prevented. As well as facilitating the exposed portion serving as an empty-housing indicator, this characteristic of the anchor-handling device discourages and/or prevents the operator from returning a previously-removed anchor into the device, e.g., thereby ensuring that only sterile anchors are disposed within the device.

For some applications, the anchor-handling devices described herein are configured to be at least in part submerged in saline prior to and/or during use, e.g., to reduce a likelihood of air (e.g., bubbles) being retained by the anchor and/or driver and subsequently introduced into the subject.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Further, the techniques, methods, operations, steps, etc. described herein can be performed on a living animal or on a non-living simulation, such as on a cadaver, cadaver heart, simulator (e.g. with the body parts, tissue, etc. being simulated), etc.

The invention claimed is:

1. An apparatus for use with a tissue anchor and an anchor driver, the apparatus comprising:
 a housing, shaped to define a channel, the channel:
  having (i) an anchor-storage zone, and (ii) a proximal opening configured to provide access for the anchor driver to the anchor-storage zone, and
  configured to enable sliding of the tissue anchor therewithin to be stored in the anchor-storage zone; and
 a retaining member:
  shaped to define a cradle for cradling and holding the tissue anchor in the anchor-storage zone, and comprising a pillar pivotable with respect to the cradle, and configured to support the tissue anchor at the cradle.

2. The apparatus according to claim 1, further comprising the tissue anchor, wherein the tissue anchor is shaped to define a core and a tissue-engaging member.

3. The apparatus according to claim 2, wherein the tissue-engaging member is shaped to define a lumen, and wherein the pillar fits within the lumen of the tissue-engaging member.

4. The apparatus according to claim 2, wherein the tissue anchor is dimensioned to slide through the channel without the tissue-engaging member touching the housing.

5. The apparatus according to claim 1, wherein the retaining member further comprises a pivot coupled to the pillar, and configured to enable pivoting of the pillar angularly away from a longitudinal axis of the retaining member.

6. The apparatus according to claim 1, wherein the pillar is configured to distribute load experienced by the tissue anchor supported at the cradle.

7. The apparatus according to claim 1, wherein the cradle is shaped to define first and second slanted surfaces.

8. The apparatus according to claim 7, wherein the first and second slanted surfaces adjoin to form an apex that is aligned with a longitudinal axis of the retaining member.

9. The apparatus according to claim 7, further comprising the tissue anchor, wherein:
the tissue anchor is shaped to define a core and a tissue-engaging member, and
the first and second slanted surfaces are configured to support only the core of the tissue anchor.

10. The apparatus according to claim 7, wherein the first and second slanted surfaces are configured to abut against the tissue anchor.

11. The apparatus according to claim 1, further comprising:
a holder, shaped to define a space for receiving the housing therewithin, the holder comprising a coupling configured to reversibly couple the housing to the holder; and
a wearable article coupled to the holder, the wearable article being configured to temporarily affix the apparatus to a body part of a user.

12. The apparatus according to claim 11, wherein:
the body part is a body part selected from the group consisting of: an arm of the user, a wrist connected to the arm of the user, and a hand connected to the arm of the user, and
the holder is oriented with respect to the wearable article such that when the wearable article is affixed to the selected body part, the holder is oriented to hold the housing in an orientation in which a longitudinal axis of the retaining member is substantially parallel with the arm of the user.

13. The apparatus according to claim 11, wherein the holder is shaped to receive the housing via a first end of the holder, and is further shaped to receive the housing via a second end of the holder, the second end being opposite the first end.

14. The apparatus according to claim 11, wherein the wearable article comprises a rigid material at least in a vicinity of the holder.

15. The apparatus according to claim 11, wherein the wearable article comprises a band having a first portion that terminates at a first end, and a second portion that terminates at a second end.

16. The apparatus according to claim 15, wherein the first end and the second end are separable by an adjustment mechanism comprising a spring-loaded coupling that enables the first portion and the second portion of the band to be moved apart from each other.

17. The apparatus according to claim 16, wherein the spring-loaded coupling is configured to bias the first portion and the second portion of the band towards each other, thereby facilitating a snug coupling of the apparatus to the body part.

18. The apparatus according to claim 1, wherein:
the housing is shaped to define a chamber that is in fluid communication with the channel, the chamber having a longitudinal axis, and
at least part of the retaining member is configured to slide within the chamber in response to a proximally-directed force applied to the tissue anchor.

19. The apparatus according to claim 18, wherein the retaining member comprises a pin configured to slide through the chamber.

20. The apparatus according to claim 19, wherein:
the housing is shaped to define first and second cavities that are in fluid communication with the chamber,
at least a portion of the retaining member is resilient,
the pin is shaped so as to define first and second legs that are compressible toward each other and toward the longitudinal axis of the chamber,
each of the first and second legs is shaped to define a respective detent, and
the apparatus is dimensioned such that when the retaining member allows the tissue anchor to leave the anchor-storage zone, further proximal movement of the retaining member causes the respective detents of the first and second legs to move into the first and second cavities, respectively.

21. The apparatus according to claim 1, further comprising the anchor driver.

22. An apparatus for use with a tissue anchor and an anchor driver, the apparatus comprising:
a housing, shaped to define a channel, the channel:
having (i) an anchor-storage zone and (ii) a proximal opening configured to provide access for the anchor driver to the anchor-storage zone, and
configured to enable sliding of the tissue anchor therewithin to be stored in the anchor-storage zone; and
a retaining member:
shaped to define a cradle for cradling and holding the tissue anchor in the anchor-storage zone,
having a retaining state in which the retaining member is configured to retain the tissue anchor in the anchor-storage zone,
being disposed within the housing such that sliding of the tissue anchor proximally out of the anchor-storage zone and through the channel causes the retaining member to slide proximally, and
comprising a pillar configured to support the tissue anchor at the cradle.

23. The apparatus according to claim 22, wherein the pillar is pivotable with respect to the cradle.

24. The apparatus according to claim 22, further comprising the tissue anchor, stored in the anchor-storage zone.

25. The apparatus according to claim 22, further comprising the anchor driver.

* * * * *